United States Patent
Kondo et al.

(10) Patent No.: US 10,563,201 B2
(45) Date of Patent: Feb. 18, 2020

(54) METHOD FOR TREATMENT OF SUBJECTS WITH TUG1 GENE EXPRESSING BRAIN TUMOR

(71) Applicant: PUBLIC UNIVERSITY CORPORATION NAGOYA CITY UNIVERSITY, Nagoya-shi, Aichi (JP)

(72) Inventors: Yutaka Kondo, Nagoya (JP); Keisuke Katsushima, Nagoya (JP)

(73) Assignee: PUBLIC UNIVERSITY CORPORATION NAGOYA CITY UNIVERSITY, Nagoya-Shi, Aichi (JP)

( * ) Notice: Subject to any disclaimer, the term of this patent is extended or adjusted under 35 U.S.C. 154(b) by 0 days.

(21) Appl. No.: 15/549,803

(22) PCT Filed: Feb. 10, 2016

(86) PCT No.: PCT/JP2016/053960
§ 371 (c)(1),
(2) Date: Nov. 10, 2017

(87) PCT Pub. No.: WO2016/129633
PCT Pub. Date: Aug. 18, 2016

(65) Prior Publication Data
US 2018/0163208 A1    Jun. 14, 2018

(30) Foreign Application Priority Data
Feb. 10, 2015   (JP) ................. 2015-024713

(51) Int. Cl.
| | | |
|---|---|---|
| C12N 15/11 | (2006.01) | |
| C12N 15/113 | (2010.01) | |
| A61P 35/00 | (2006.01) | |
| A61K 48/00 | (2006.01) | |
| A61K 31/713 | (2006.01) | |
| A61K 31/7105 | (2006.01) | |
| A61K 31/7125 | (2006.01) | |
| A61K 35/76 | (2015.01) | |
| A61P 35/02 | (2006.01) | |

(52) U.S. Cl.
CPC ........ *C12N 15/1135* (2013.01); *A61K 31/713* (2013.01); *A61K 31/7105* (2013.01); *A61K 31/7125* (2013.01); *A61K 35/76* (2013.01); *A61K 48/00* (2013.01); *A61P 35/00* (2018.01); *A61P 35/02* (2018.01); *C12N 15/113* (2013.01); *C12N 2310/11* (2013.01); *C12N 2310/14* (2013.01); *C12N 2310/3519* (2013.01)

(58) Field of Classification Search
None
See application file for complete search history.

(56) References Cited

U.S. PATENT DOCUMENTS

| | | | | |
|---|---|---|---|---|
| 2005/0261216 A1* | 11/2005 | Lollo | ................... | C12N 15/113 514/44 A |
| 2008/0167265 A1* | 7/2008 | Freier | ................ | C12N 15/1138 514/44 A |
| 2015/0329858 A1 | 11/2015 | Aburatani et al. | | |

FOREIGN PATENT DOCUMENTS

WO   WO 2014/077354 A1   5/2014

OTHER PUBLICATIONS

Nakamori et al., Stabilization of expanded (CTG)*(CAG) repeats by antisense oligonucleotides, Molecular Therapy, vol. 19, pp. 2222-2227. (Year: 2011).*
Cai, H. et al., "The Long Noncoding RNA TUG1 Regulates Blood-Tumor Barrier Permeability by Targeting miR-144", *Oncotarget*, vol. 6, No. 23, pp. 19759-19779.
Han, Y. et al., "Long Intergenic Non-Coding RNA TUG1 is Overexpressed in Urothelial Carcinoma of the Bladder", *Journal of Surgical Oncology*, No. 107, 2013, pp. 555-559.
Huang, M. et al., "Long Non-Coding RNA TUG1 is Up-Regulated in Hepatocellular Carcinoma and Promotes Cell Growth and Apoptosis by Epigenetically Silencing of KLF2", *Molecular Cancer*, vol. 14, 2015, 12 pages.
Khalil, "Many Human Large Intergenic Noncoding RNAs Associate With Chromatin-Modifying Complexes and Affect Gene Expression", *PNAS*, Jul. 14, 2009, vol. 106, No. 28, pp. 11667-11672.
Meseure, D. et al., "Biopathological Signification of the Long Intergenic Non Coding RNA TUG1 Dysregulation Across Invasive Breast Carcinomas", *Modern Pathology*, vol. 27, No. S2, 2014, pp. 68A.
Sun, J. et al., "The Long Non-Coding RNA TUG1 Indicates a Poor Prognosis for Colorectal Cancer and Promotes Metastasis by Affecting Epithelial-Mesenchymal Transition", *Journal of Translational Medicine*, vol. 14, No. 42, 2016, 10 pages.
Tan, J. et al., "Double-Negative Feedback Loop Between Long Non-Coding RNA TUG1 and miR-145 promotes Epithelial to Mesenchymal Transition and Radioresistance in Human Bladder Cancer Cells", *FEBS Letters*, vol. 589, 2015, pp. 3175-3181.
Xu, Y. et al., "Upregulation of the Long Noncoding RNA TUG1 Promotes Proliferation and Migration of Esophageal Squamous Cell Carcinoma", *Tumor Biol.*, No. 36, 2015, pp. 1643-1651.

(Continued)

*Primary Examiner* — Dana H Shin
(74) *Attorney, Agent, or Firm* — Brinks Gilson & Lione

(57) ABSTRACT

This invention provides a composition and a method for treating or preventing a subject having a tumor that more highly expresses a TUG1 gene than in normal tissues (e.g., brain tumor, breast cancer, colon cancer, prostate cancer, liver cancer, lung cancer, leukemia, or lymphoma), which composition comprises, as an active ingredient, a nucleic acid that inhibits the high expression of the TUG1 gene in tumor stem cells.

7 Claims, 13 Drawing Sheets

Specification includes a Sequence Listing.

(56) References Cited

OTHER PUBLICATIONS

Young, T. et al., "The Noncoding RNA Taurine Upregulated Gene 1 is Required for Differentiation of the Murine Retina", *Current Biology*, vol. 16, Mar. 29, 2005, pp. 501-512.

Zhang, E. et al., "P53-Regulated Long Non-Coding RNA TUG1 Affects Cell Proliferation in Human Non-Small Cell Lung Cancer, Partly Through Epigenetically Regulating HOXB7 Expression", *Cell Death & Disease.*, No. 5, May 2014, 12 pages.

Zhang, Q. et al., "Down-Regulation of Long Non-Coding RNA TUG1 Inhibits Osteosarcoma Cell Proliferation and Promotes Apoptosis", *Asian Pacific J Cancer Prev*, vol. 14, No. 4, 2013, pp. 2311-2315.

International Search Report in corresponding International Application No. PCT/JP2016/053960, dated Apr. 12, 2016, 6 pages.

Cai, H., "The long noncoding RNA TUG1 regulates blood-tumor barrier permeability by targeting miR-144," *Oncotarget*, 6(23):19759-19779 (2015).

Han, Y., et al., "Long Intergenic Non-Coding RNA TUG1 is Overexpressed in Urothelial Carcinoma of the Bladder," *Journal of Surgical Oncology*, 107:555-559 (2013).

Huang, M-D., et al., "Long non-coding RNA TUG1 is up-regulated in hepatocellular carcinoma and promotes cell growth and apoptosis by epigenetically silencing of KLF2," *Molecular Cancer*, 14:165, 12 pages (2015).

International Search Report received in PCT Application No. PCT/JP2016/053960 dated Apr. 12, 2016.

Khalil, A.M., et al., "Many human large intergenic noncoding RNAs associate with chromatin-modifying complexes and affect gene expression," *PNAS*, 106(28):11667-11672 (2009).

Meseure, D., et al., "Biopathological Signfication of the Long Intergenic Non Coding RNA TUG1 Dysregulation across Invasive Breat Carcinomas," Curie Institute, Paris, France, Annual Meeting Abstracts, p. 68A (2014).

Sun, J., et al., "The long non-coding RNA TUG1 indicates a poor prognosis for colorectal cancer and promotes metastasis by affecting epithelial-mesenchymal transition," *Journal of Translation Medicine*, 14:42, 10 pages (2016).

Tan, J., et al., "Double-negative feedback loop between long non-coding RNA TUG1 and miR-145 promotes epithelial to mesenchymal transition and radioresistance in human bladder cancer cells," FEBS Letters, 589:3175-3181 (2015).

Xu, Y., et al., "Upregulation of the long noncoding RNA TUG1 promotes proliferation and migration of esophageal squamous cell carcinoma," *Tumor Biol.*, 36:1643-1651 (2015).

Young, T.L., et al., "The Noncoding RNA Taurine Upregulated Gene 1 Is Required for Differentiation of the Murine Retina," *Current Biology*, vol. 15:501-512 (2005).

Zhang, E-b., et al., "P53-regulated long non-coding RNA TUG1 affects proliferation in human non-small cell lung cancer, partly through epigenetically regulating HOXB7 expression," *Cell Death & Disease*, 5(5):e1243, 12 pages (2014).

Zhang, Q, et al., "Down-regulation of Long Non-coding RNA TUG1 Inhibits Osteosarcoma Cell Proliferation and Promotes Apoptosis," *Asian Pacific Journal of Cancer Prevention*, 14(4):2311-2315 (2013).

\* cited by examiner

| Sequence | Antisense strand (5'→3') | | Sense strand (5'→3') | | Remarks |
|---|---|---|---|---|---|
| si-TUG1 #1 | UGAUUCUUAACUCUCUdCdG | (SEQ ID NO: 28) | CCAGAAGAGUUAAGAAUCdA | (SEQ ID NO: 20) | PNAS106:11667-11672,2009 |
| si-TUG1 #2 | UUACUCUGGGCUUCUGCdAdC | (SEQ ID NO: 29) | GUGCAGAAGCCCAGAGUdAdA | (SEQ ID NO: 21) | PNAS106:11667-11672,2009 |
| si-TUG1 #3 | UUGUUCUCUGGCUAUAUCCdCdA | (SEQ ID NO: 30) | GGAUAUAGCCAGAGAACAAdTdT | (SEQ ID NO: 22) | PNAS106:11667-11672,2009 |
| si-TUG1 #4 | ACGAUAAUUCUUCUUAACdAdA | (SEQ ID NO: 31) | GUUAAGAAGAAUUAUCGUdCdA | (SEQ ID NO: 23) | |
| si-TUG1 #5 | AUUAAUAACUAAAAAUCCdCdC | (SEQ ID NO: 32) | GGAUUUUUAGUUAUUAAUdGdC | (SEQ ID NO: 24) | |
| si-TUG1 #6 | UGAAUUUCAUUCAUUGAGdAdT | (SEQ ID NO: 33) | CUCAAAUGAUGAAUUCAdTdG | (SEQ ID NO: 25) | |
| si-TUG1 #7 | UUGAAGUAGAAAAACAGGdGdT | (SEQ ID NO: 34) | CCCUGUUUUUCUACUUCAAdAdT | (SEQ ID NO: 26) | |
| si-TUG1 #8 | AGAAUUCUUACAUUUGUGdTdA | (SEQ ID NO: 35) | CACAAAUGUAAGAAUUCUdAdC | (SEQ ID NO: 27) | |

B

| Sequence | Antisense strand (5'→3') | | Sense strand (5'→3') | | Remarks |
|---|---|---|---|---|---|
| si-TUG1 #9 | GCCAUUUAAACAGAAACAGUAdCdC | (SEQ ID NO: 45) | UACUGUUUCUUUAAAUGGCdGdG | (SEQ ID NO: 39) | |
| si-TUG1 #10 | GAUUCAAAGCUAAACUUUUdTdC | (SEQ ID NO: 46) | AAAAGUUUAGCUUUGAAUCdAdC | (SEQ ID NO: 40) | |
| si-TUG1 #11 | CAUUCAAGAUGCAUUUAUdAdA | (SEQ ID NO: 47) | AUAAAUGCAUCUUGAUAUGdTdT | (SEQ ID NO: 41) | |
| si-TUG1 #12 | GGAUUUUUAGUUAUUAAUdGdC | (SEQ ID NO: 48) | AUUAAUAACUAAAAAUCCdCdC | (SEQ ID NO: 42) | |
| si-TUG1 #13 | UAAUCCAUAGGGCUUAUdTdC | (SEQ ID NO: 49) | GAAUAAGCCCUAUGGAUUdAdA | (SEQ ID NO: 43) | PNAS106:11667-11672,2009 |
| si-TUG1 #14 | CCCUUUUUUGCUUAAGUUAdCdT | (SEQ ID NO: 50) | UAACUUAAGCAAAAAGGGdTdA | (SEQ ID NO: 44) | |

Fig. 6

| Sequence | Antisense strand (5'→3') | |
|---|---|---|
| LNA-TUG1-1 #1 | UUACUCUGGGCUUCUGCAC | (SEQ ID NO: 36) |
| LNA-TUG1-1 #2 | UUACUCUGGGCUUCUGCAC | (SEQ ID NO: 37) |
| LNA-TUG1-1 #3 | UUACUCUGGGCUUCUGCAC | (SEQ ID NO: 38) |

Fig. 9

| Sequence | Antisense strand (5'→3') | |
|---|---|---|
| LNA-TUG1-2 #1 | UGAAUUUCAAUCAUUUGAGAU | (SEQ ID NO: 51) |
| LNA-TUG1-2 #2 | UGAAUUUCAAUCAUUUGAGAU | (SEQ ID NO: 52) |
| LNA-TUG1-2 #3 | UGAAUUUCAAUCAUUUGAGAU | (SEQ ID NO: 53) |

METHOD FOR TREATMENT OF SUBJECTS WITH TUG1 GENE EXPRESSING BRAIN TUMOR

This application is a 371 application of PCT/JP2016/053960 having an international filing date of Feb. 10, 2016, which claims priority to Japanese Patent Application No. 2015-024713 filed Feb. 10, 2015, the entire contents of which are incorporated herein by reference.

TECHNICAL FIELD

The present invention relates to an anti-tumor agent against a tumor that expresses the TUG1 gene at a high level.

BACKGROUND ART

The taurine upregulated gene 1 is abbreviated as "TUG1," which is a spliced and polyadenylated RNA that was identified as non-coding RNA necessary for differentiation of rodents' retinas by Young et al. (Non-Patent Literature 1) and others, and TUG1 is expressed at a high level in tissues in the nervous system, such as retinal or brain tissues.

Concerning the roles of TUG1 in cancers or tumors, for example, cell growth is accelerated upon TUG1 knockdown in non-small cell lung cancer (NSCLC), as disclosed by Zhang et al. (Non-Patent Literature 2). In contrast, it has been reported that TUG1 is overexpressed in particular types of cancers or tumors and inhibition of TUG1 expression leads to inhibition of growth thereof. For example, Xu et al. (Non-Patent Literature 3) describes that TUG1 silencing leads to inhibition of esophageal squamous cell cancer (ESCC) cell growth and inhibition of cell cycle progression. Also, Zhang et al. (Non-Patent Literature 4) describes that TUG1 is overexpressed in osteosarcoma cell lines and that inhibition of TUG1 expression causes apoptosis of osteosarcoma cells. In addition, Han et al. (Non-Patent Literature 5) describes that TUG1 is overexpressed in urothelial cancer, TUG1 is correlated with an advanced clinical stage, and TUG1 silencing results in growth inhibition and apoptosis induction to the cancer.

CITATION LIST

Non-Patent Literature

Non-Patent Literature 1: T. L. Young et al., Curr. Biol., 15 (6): 501-512, 2005
Non-Patent Literature 2: E. B. Zhang et al., Cell Death Dis., 2014 May, 22; 5:e1243.doi:10.1038/cddis.2014.201
Non-Patent Literature 3: Y. Xu et al., Tumor Biology Oct. 31, 2014, doi: 10, 1007/s13277.014.2763.6
Non-Patent Literature 4: Q. Zhang et al., Asian Pacific J Cancer Prev, 14 (4): 2311-2315, 2013
Non-Patent Literature 5: Y. Han et al., J. Surg. Oncol., 107: 555-559, 2013

SUMMARY OF INVENTION

Technical Problem

An object of the present invention is to provide nucleic acid drugs that enable prevention or treatment of cancer or tumors that express TUG1 at high levels, including brain tumors, such as glioblastoma (GBM).

GBM is the most malignant tumor among primary brain tumors, and it remains very difficult to achieve amelioration or radical treatment. GBM has abnormalities in the epigenome, such as non-translational RNA, histone modification, or DNA methylation, in addition to abnormalities in the genome. It is suggested that such abnormalities in the epigenome give rise to malignancy of GBM.

The present inventors have now found that TUG1, which is a type of lncRNA (long noncoding RNA), is highly expressed in several tumors including GBM, and TUG1-targeting nucleic acids are effective for significant regression of such tumors, thereby leading to the completion of the invention.

Solution to Problem

Accordingly, the present invention encompasses the following features.

[1] A composition for treatment or prevention of a subject having a tumor that expresses a TUG1 gene more highly than in normal tissues, comprising, as an active ingredient, a nucleic acid that inhibits the high expression of the TUG1 gene in stem cells of the tumor.

[2] The composition according to [1], wherein the nucleic acid is a siRNA, a precursor RNA of the siRNA, an anti-sense RNA, or a modified RNA thereof, or an antisense DNA, each being to a transcript RNA of the TUG1 gene.

[3] The composition according to [1] or [2], wherein the nucleic acid targets a region of the nucleotide numbers 1044 to 1062, 1044 to 1062, or 1044 to 1062 (which is the region of #1 in FIG. 2) and/or a region of the nucleotide numbers 2997 to 5181, 2941 to 5111, or 2941 to 5125 (which is the region of #5 to #4 in FIG. 2) in the nucleotide sequence of SEQ ID NO: 1, 2, or 3 of the transcript RNA of the TUG1 gene, respectively.

[4] The composition according to any of [1] to [3], wherein the nucleic acid is one of or a combination of two or more of: siRNAs each comprising a sense strand consisting of the nucleotide sequence of any of SEQ ID NOs: 4 to 11 and an antisense strand consisting of the nucleotide sequence of any of SEQ ID NOs: 12 to 19 complementary to the sense strand respectively; precursor RNAs of the siRNAs; or modified RNAs thereof.

[5] The composition according to any of [2] to [4], wherein the modified RNA comprises one or two or more modified nucleotides or deoxyribonucleotides.

[6] The composition according to [5], wherein the modified RNA comprising the deoxyribonucleotides(s) is a siRNA comprising a sense strand consisting of the nucleotide sequence of any of SEQ ID NOs: 20 to 27 and an antisense strand consisting of the nucleotide sequence of any of SEQ ID NOs: 28 to 35 complementary to the sense strand respectively, or an antisense RNA/DNA chimera consisting of the nucleotide sequence of any of SEQ ID NOs: 28 to 35.

[7] The composition according to [5], wherein the modified RNA comprising the modified nucleotide(s) is a LNA-modified antisense RNA comprising at least two LNA-modified nucleotides that have a 2'-O,4'-C methylene bridge at each end by which the nucleotides are locked.

[8] The composition according to any of [2], [3], and [5] to [7], wherein the modified RNA is a LNA-modified antisense RNA consisting of the nucleotide sequence of any of SEQ ID NO: 36 to 38 and 51 to 53.

[9] The composition according to any of [1] to [6], wherein the nucleic acid is a vector comprising: DNA encoding siRNA, precursor RNA of the siRNA, or antisense RNA, each RNA being to the transcript RNA of the TUG1 gene; or antisense DNA being to the transcript RNA of the TUG1 gene.

[10] The composition according to any of [1] to [9], wherein the tumor is selected from the group consisting of brain tumor, breast cancer, colon cancer, prostate cancer, liver cancer, lung cancer, leukemia, and lymphoma.

[11] A method for treatment of a subject who has a tumor more highly expressing the TUG1 gene than in normal tissues, comprising administering the composition according to any of [1] to [10] to the subject.

[12] The method according to [11], wherein the tumor is selected from the group consisting of brain tumor, breast cancer, colon cancer, prostate cancer, liver cancer, lung cancer, leukemia, and lymphoma.

The present invention enables inhibition of the growth of tumor stem cells in tumors more highly expressing the TUG1 gene than in normal tissues, such as brain tumor, breast cancer, colon cancer, prostate cancer, liver cancer, lung cancer, leukemia, and lymphoma, thereby exerting effects of tumor regression and suppression of tumor metastasis.

This description includes the contents disclosed in Japanese Patent Application No. 2015-024713 from which the present application claims priority.

BRIEF DESCRIPTION OF DRAWINGS

FIG. 3 shows the nucleotide sequences (i.e., sense strand sequences and antisense strand sequences) of si-TUG1#1 to si-TUG1#14 tested in FIG. 2. siRNAs that have exerted inhibitory effects are si-TUG1#1 to si-TUG1#8 (FIG. 3A), while si-TUG1#9 to si-TUG1#14 exerted low or no inhibitor effects (FIG. 3B).

FIG. 6 shows LNA-modified antisense RNAs prepared based on the nucleotide sequence of SEQ ID NO: 13; i.e., LNA-TUG1-1#1 (SEQ ID NO: 36), LNA-TUG1-1#2 (SEQ ID NO: 37), and LNA-TUG1-1#3 (SEQ ID NO: 38). LNA-modified sites are underlined.

FIG. 9 shows LNA-modified antisense RNAs prepared on the basis of the nucleotide sequence of SEQ ID NO: 17; i.e., LNA-TUG1-2#1 (SEQ ID NO: 51), LNA-TUG1-2#2 (SEQ ID NO: 52), and LNA-TUG1-2#3 (SEQ ID NO: 53). LNA-modified sites are underlined.

FIG. 12A shows the TUG1 expression levels in the PC3 cell line when si-TUG1#2 or control siRNA ("NC") was allowed to act on the cell line, and FIG. 12B shows the relative cell growth rate of the PC3 cell line when each of the siRNAs was allowed to act thereon. The symbol "*" indicates statistical significance of p<0.01.

DESCRIPTION OF EMBODIMENTS

Figure 1:
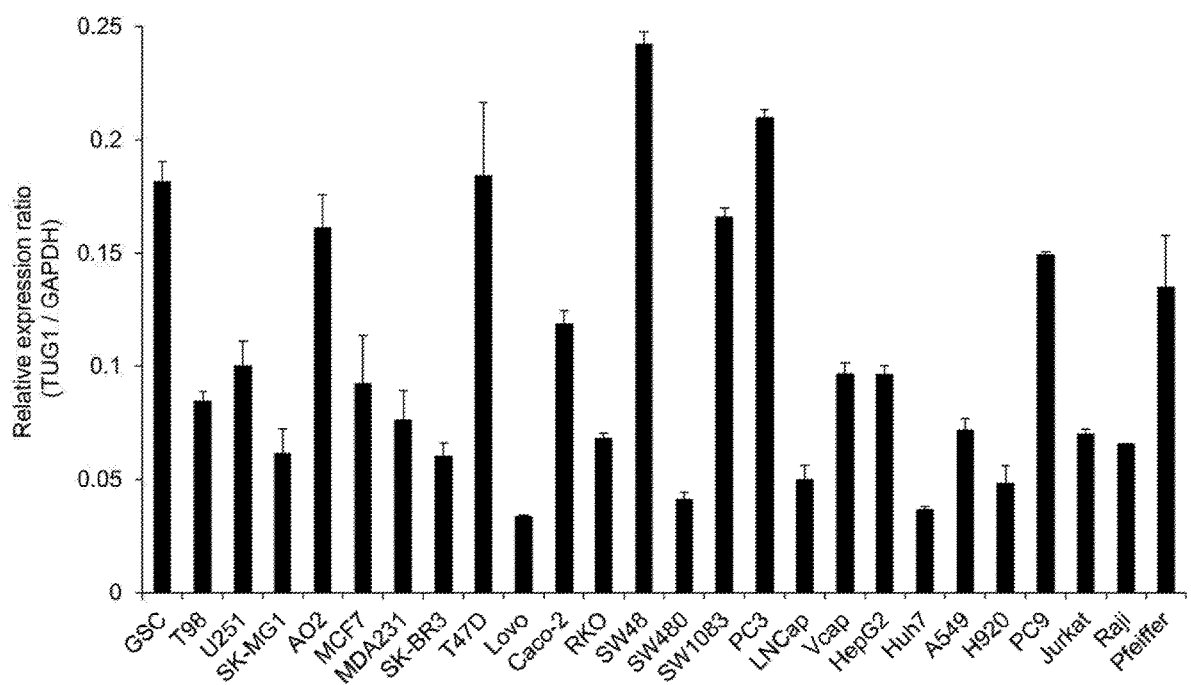
FIG. 1 shows TUG1 expression levels in various tumor cell lines. In the figure, GSC represents a glioma stem cell line; T98, U251, SK-MG1, and AO2 represent glioma cell lines; MCF7, MDA231, SK-BR3, and T47D represent breast cancer cell lines; Lovo, Caco-2, RKO, SW48, SW480, and SW1083 represent colon cancer cell lines; PC3, LNCap, and Vcap represent prostate cancer cell lines; HepG2, Huh7, and A549 each represent liver cancer cell lines; H920 and PC9 represent lung cancer cell lines; Jurkat represents a leukemia cell line; Raji represents a Burkitt's lymphoma cell line; and Pfeiffer represents a lymphoma cell line. The TUG1 expression levels are relative to the internal standard GAPDH.

In recent years, the relationship between abnormal expression of Non-coding RNAs and cancers has drawn attention. In particular, many microRNAs (miRNAs) have been discovered in the field of cancer diagnosis. While miRNA types vary depending on cancer or tumor types, some miRNAs are overexpressed, and some other miRNAs are expressed at decreased levels, in comparison with normal cells. Accordingly, such relationship becomes complicated. In addition, the number of reports concerning long non-coding RNA (lncRNA) is smaller than that concerning miRNA, and both situations in which overexpression is observed and decreased expression is observed are known concerning the relationship between lncRNAs and cancers.

The present inventors have engaged in the development of therapeutic agents for brain tumor, which is difficult to treat among various types of tumors. Glioblastoma (GBM) is the most malignant tumor among primary brain tumors and is very difficult in its amelioration. GBM has abnormalities in the epigenome such as non-translational RNA, histone modification, or DNA methylation, in addition to abnormalities in the genome. It is suggested that such abnormalities in the epigenome give rise to malignancy of GBM. Gene expression control of lncRNA, which is one of non-translational RNAs, is deeply associated with various vital phenomena, such as cell differentiation or cell growth, and the relationship of vital phenomena with malignancy of cancers has also been reported in recent years (R. A. Gupta et al., Nature, 464: 1071-1076, 2010; L. Yang et al., Nature, 500: 598-602, 2013; J. H. Yuan et al. Cancer Cell, 25: 666-681, 2014; A. M. Khalil et al., PNAS, 106: 11667-11672, 2009).

The present inventors have now found that TUG1, a type of lncRNA, is more highly expressed in glioma stem cells (GSC) established from human GBM than in normal cells, and inhibition of TUG1 expression is led to inhibition of GSC growth. In addition, the present inventors have also now found that nucleic acid drugs that target TUG1, are effective for treatment of GBM. On the basis of such findings, the present inventors have further now found that TUG1 is also expressed at high levels in several tumors which were not reported in the past, and that the nucleic acid drugs, which target tumor stem cells, could be expected to exert anti-tumor effects on such tumors as with the case of GSC.

As described in the BACKGROUND ART above, it is known that TUG1 expression levels vary depending on tumor types; however, whether or not inhibition of TUG1 expression is effective for treatment of particular types of tumors that highly express TUG1 has not been sufficiently verified. In addition, there have been no reports concerning the relationship between TUG1 and tumor stem cells.

TUG1 plays a role in suppressing a particular type of gene which is induced by p53 and is associated with the cell cycle, and it is hypothesized that lncRNAs, including TUG1, function in a tumor-growth-inhibiting manner in the p53 transcription pathway, although details thereof remain unknown (A. M. Khalil et al., PNAS, 106: 11667-11672, 2009).

Under the above circumstances, the present inventors have now found that the growth of several tumors, including brain tumor, is inhibited as a result of the inhibition of TUG1 expression in tumor stem cells. Specifically, the present invention is characterized by the composition comprising, as an active ingredient, a nucleic acid that inhibits high expression of the TUG1 gene in tumor stem cells, which is used for treatment or prevention of, for example, brain tumor, breast cancer, colon cancer, prostate cancer, liver cancer, lung cancer, leukemia, or lymphoma in a subject having a tumor that expresses the TUG1 gene more highly than in normal tissues.

Hereafter, the present invention will be described in more detail.

1. Nucleic Acid that Inhibits High Expression of the TUG1 Gene

The composition of the present invention comprises, as an active ingredient, a nucleic acid that inhibits high expression of the TUG1 gene in tumor stem cells.

Concerning the term " . . . inhibits high-level expression of the TUG1 gene" used herein, an expression level that is abnormally higher than the level (or amount) of TUG1 that is normally expressed in normal tissues (or normal cells) is referred to as "high expression." Such term refers to a meaning that the high expression of the TUG1 gene is inhibited to a normal level or lower and that the function of the lncRNA, which is a TUG1 gene transcript, is suppressed. In the present invention, the function of lncRNA is associated with the growth, progression, or metastasis of a cancer or tumor. In the present invention, a nucleic acid that inhibits high expression of the TUG1 gene in tumor stem cells is administered to a subject, so as to inhibit TUG1 expression in the subject having a tumor, such as brain tumor, breast cancer, colon cancer, prostate cancer, liver cancer, lung cancer, leukemia, or lymphoma, thereby inhibiting the growth of such tumors.

The subject is not particularly limited, as long as it is an animal. Preferably the subject is a mammalian animal, such as a human, dog, cat, horse, cattle or cow, or any of other types of mammalian animals raised, for example, at zoos, more preferably a human. Among such animals, a subject having a tumor that highly expresses the TUG1 gene is the target animal of the present invention.

TUG1 is from any of the animals described above. For example, TUG1 consists of the nucleotide sequence of NR_110492 (SEQ ID NO: 1), NR_110493 (SEQ ID NO: 2), or NR_002323 (SEQ ID NO: 3) known as a human TUG1 gene transcript (i.e., a long non-coding RNA ), or TUG1 is a naturally occurring variant consisting of a nucleotide sequence comprising a deletion(s), a substitution(s), an addition(s), or an insertion(s) of one or several nucleotides in the nucleotide sequence above, or a nucleotide sequence having 70% or higher, 80% or higher, or 90% or higher, preferably 95% or higher, more preferably 98% or higher or, 99% or higher, sequence identity to the nucleotide sequence described above.

The term "several" used herein refers to an integer of 2 to 10, preferably 2 to 5. The sequence identity may be determined with the use of conventional algorithms, including BLAST, to make a sequence alignment of nucleotide sequences.

In the present invention, the nucleic acids that inhibit high expression of the TUG1 gene include siRNAs having the effect of RNA interference (RNAi) or precursor RNAs of the siRNAs, or modified RNAs thereof, or vectors comprising a DNA encoding a siRNA to the transcript RNA of the TUG1 gene or encoding a precursor RNA of the siRNA. Other examples of the nucleic acids include antisense RNAs or antisense DNAs, vectors comprising DNAs encoding the antisense RNAs or antisense DNAs, or modified nucleic acids thereof.

In the present invention, the type or sequence of the nucleic acid is not particularly limited, as long as the nucleic acid inhibits high expression of the TUG1 gene and inhibits the tumor growth in tumor stem cells. The nucleic acid preferably targets a region within the nucleotide sequence of the transcript RNA of the TUG1 gene of the subject, for example, a region of the nucleotide numbers 1044 to 1062, 1044 to 1062, or 1044 to 1062 (which is the region of #1 in FIG. 2) and/or regions of the nucleotide numbers 2997 to 5181, 2941 to 5111, or 2941 to 5125 (which is the region of #5 to #4 in FIG. 2) in the nucleotide sequence of the transcript RNA of the human TUG1 gene, such as the nucleotide sequence of SEQ ID NO: 1, 2 or 3.

Concerning siRNAs that exert the RNAi effect on TUG1 or their precursor RNAs, each siRNA is a double-stranded RNA consisting of a sense RNA and an antisense RNA, which consists of a sequence of 18 to 25 nucleotides, preferably 20 to 24 nucleotides, further preferably 21 to 23 nucleotides complementary to a part of the transcript RNA of the TUG1 gene and exerting the RNA interference (RNAi) effect. Sense RNA and antisense RNA may each have, at its 3' end, an overhang of 2 to 5 nucleotides, preferably 2 nucleotides, such as UU (TT in the case of DNA). It is suggested that the overhang might interact with RISC (W. R. Strapps et al., Nucleic Acids Res. 2010 August; 38 (14): 4788-4797).

The term "RNAi effect" has the meaning generally used in the art; i.e., it is the phenomenon that a short double-stranded RNA (siRNA) degrades a target transcript RNA in a nucleotide-sequence-specific manner so as to inhibit the gene expression.

The precursor RNA is any of priRNA, preRNA, and shRNA of the siRNA. The priRNA has a transcript RNA sequence for the TUG1 gene, such as the nucleotide sequence of SEQ ID NO: 1, 2 or 3. The preRNA is a preshRNA produced by enzymatic processing of priRNA. The shRNA is an abbreviation of "short hairpin RNA," which is produced enzymatically from the preshRNA and consists of: a stem of sense and antisense strands having the same sequences as siRNA; and a hairpin-loop. The hairpin structure of shRNA is cleaved into siRNA by the cellular mechanism, then the siRNA is bound to an RNA-induced silencing complex (RISC), and the resulting complex binds to a transcript RNA having a sequence complementary to the siRNA, tor cleavage of the transcript RNA.

The nucleic acid of the present invention is, for example, a single siRNA or a combination of two or more siRNAs, where the siRNA comprises a sense strand consisting of the nucleotide sequence of any of SEQ ID NOs: 4 to 11 and an antisense strand consisting of the nucleotide sequence of any of SEQ ID NOs: 12 to 19 complementary to the sense strand, respectively.

Alternatively, the nucleic acid of the present invention is a vector comprising a DNA encoding the siRNA, a precursor RNA of the siRNA, or an antisense RNA, to the transcript RNA of the TUG1 gene, or a vector comprising an antisense DNA. The precursor RNA is preferably a shRNA.

The vector comprises a regulatory sequence capable of expressing the DNA when introduced into a cell. The vector is, for example, a virus vector, such as adeno-associated virus, retrovirus, lentivirus, or Sendai virus, or a non-virus vector, such as plasmid, artificial chromosome (e.g., bacterial artificial chromosome (BAC), yeast artificial chromosome (YAC), human artificial chromosome (HAC), or mouse artificial chromosome (MAC)). From the viewpoint of safety, a preferable vector is, for example, a plasmid, a Sendai virus vector, or an adeno-associated virus vector. The plasmid is preferably a plasmid that can be used in a mammalian 1 cell, preferably human cell, and is verified for its safety. Specific examples of the plasmid vectors include, but are not limited to, vectors as described in JP 2014-508515 A, such as non-virus vectors, for example pSilencer 4.1-CMV (Ambion), pcDNA3, pcDNA3.1/hyg, pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCl, pSVL, pKSV-10, pBPV-1, pML2d, and pTDT1.

The regulatory sequence can comprise a promoter, a transcription initiation site, a terminator, and the like, and where needed, an enhancer, a selection marker sequence, and the like. For the promoter, any endogenous or exogenous promoter can be used, as long as it promotes the initiation of DNA transcription in a certain host cell. For example, it is an U6 or H1 promoter. Thus, the vector can be constantly expressed after it is introduced into a cell, and the vector is transmitted to daughter cells together with the effect of gene silencing.

In general, RNA is easily degraded by ribonucleases in, for example, the blood or the like in vivo, thus being extremely unstable. In order to overcome such problem, in the present invention, nucleotides of sense and antisense strands are preferably modified. Examples of modifications include a modification(s) of at least one nucleotide, preferably a plurality of nucleotides, such as modifications of bases, modifications of sugars, modifications of phosphoric diester portions, a combination thereof, and/or a cyclic structure comprising a double-stranded stem and 2 loops, and a chimeric structure comprising DNA. Examples of such modifications include, but are not limited to, the following modifications.

Both RNA and DNA are nucleic acids composed of a chain or chains of nucleotides comprising sugars, bases, and phosphodiester linkages. Structural differences between such nucleic acids are sugars in nucleotides. That is, the sugar constituting RNA is ribose and the sugar constituting DNA is 2'-deoxyribose in which the hydroxyl group at position 2' has been substituted with hydrogen. In addition, the bases constitute further differences; that is, the bases for RNA are adenine (A), uracil (U), guanine (G), and cytosine (C), while the bases for DNA are adenine (A), thymine (T), guanine (G), and cytosine (C).

Modification of the phosphoric diester portions as the backbone includes substitutions of the phosphodiester linkages with phosphorothioate, phosphorodithioate, alkyl phosphonate, or phosphoramidate linkages.

Examples of the base and sugar modifications include those exemplified in JP 2007-525192 A, such as 2'-deoxy-2'-halo (e.g., fluoro, chloro, or bromo) nucleotides, 2'-deoxy-2'-halo (e.g., fluoro, chloro, or bromo) pyrimidine nucleotides, 2'-deoxy-2'-halo (e.g., fluoro, chloro, or bromo)

cytidine nucleotides, 2'-deoxy-2'-halo (e.g., fluoro, chloro, or bromo) uridine nucleotides, 2'-deoxy-2'-halo (e.g., fluoro, chloro, or bromo) guanosine nucleotides, 2'-O-methylpurine nucleotides, 2'-deoxyribonucleotide, locked nucleic acid (LNA) such as 2'-O,4'-C methylene bridge (—O—CH$_2$—)-modified nucleotide, 2'-O,4'-C ethylene bridge (—O—CH$_2$CH$_2$—)-modified nucleotide, 2'-methoxyethyl nucleotides, 4'-thio nucleotides, 2'-methoxyethoxy (2'-MOE) nucleotides, 2'-methoxy (2'-OMe) nucleotides, 2'-deoxy-2'-chloro nucleotides, and 2'-azido nucleotides. Concerning 2'-modified nucleotides, in addition to the above examples, the position 2' of the sugar may be substituted as described in JP 2010-507579 A with, for example, halogen, allyl, amino, azido, acetoxy, alkyl, alkoxy, carboxy, acyl, carbonyloxy, benzyl, phenyl, nitro, thiol, thioalkoxy, aryl, alkenyl, alkynyl, cyano, OCN, CF$_3$, OCF$_3$, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkyl, aryl, aralkyl, O-alkyl aryl, O-aralkyl, O(CH$_2$)$_2$SCH$_3$, O—(CH$_2$)$_2$—O—N(R$_m$)(R$_n$), or O—CH$_2$—C(=O)—N(R$_m$(R$_n$), where R$_m$ and R$_n$ independently represent H, an amino protecting group, or a substituted or unsubstituted C$_1$-C$_{10}$ alkyl.

The LNA-modified nucleotide is an artificial nucleic acid developed by Takeshi Imanishi et al. (M. Abdur Rahman, Sayori Seki, Satoshi Obika, Haruhisa Yoshikawa, Kazuyuki Miyashita, Takeshi Imanishi, "Design, synthesis, and properties of 2',4'-BNA: A bridged nucleic acid analogue," J. Am. Chem. Soc., 130. 4886-4896 (2008)). In the present invention, the nucleotides with LNA (also referred to as "BNA (bridged nucleic acid)") introduced into the sugar portions of the nucleotide sequences of siRNAs would have remarkable nuclease tolerance. Examples of antisense RNAs each comprising at least 2, and preferably 3 or 4 LNA modified nucleotides at each end include modified RNAs of the nucleotide sequences (SEQ ID NO: 28 to 35) of the antisense strands shown in FIG. 3A, such as modified RNAs consisting of the nucleotide sequence as shown in any of SEQ ID NOs: 36 to 38 and SEQ ID NOs: 51 to 53, although the RNAs are not limited thereto.

The nucleic acids of the present invention may also have an RNA/DNA chimeric structure comprising a deoxyribonucleotide sequence in a part of the nucleotide sequence of siRNA. The presence of such deoxyribonucleotide sequence can provide higher nuclease tolerance when compared with only the ribonucleotide sequence (e.g., JP Patent No. 3,803, 318). The deoxyribonucleotides may account for 30% or less, preferably 20% or less of the total number of nucleotides constituting the antisense strand or the sense strand of the nucleotide sequence of siRNA. The deoxyribonucleotides may be contained in both the antisense strand and the sense strand of siRNA, or it may be contained only in the sense strand. Preferably the deoxyribonucleotide present on the 3' side in the nucleotide sequence of siRNA, and, for example, a sequence comprising 2 to 4 continuous deoxyribonucleotides may be present as an overhang at the 3' end. Specifically, the RNA/DNA chimera is a double-stranded RNA consisting of the sense strand having the nucleotide sequence of any of SEQ ID NOs: 20 to 27 and the antisense strand having the nucleotide sequence of any of SEQ ID NOs: 28 to 35.

A nucleic acid comprising the cyclic structure (i.e., the structure comprising a double-stranded stem and 2 loops) is a so-called dumbbell-shaped single-stranded RNA. The stem is composed of a sense strand sequence and an antisense strand sequence of siRNA, the sequences being complementary to each other. The loops are composed of, for example, about 2 to 15 non-complementary nucleotides per loop linked to each terminus of the stem (e.g., U.S. Pat. Nos. 5,168,053, 5,190,931, and 5,135,917, Smith and Clusel et al., 1993, Nucl. Acids Res., 21: 3405-3411, and U.S. Pat. No. 5,087,617).

Other examples of the nucleic acids include antisense RNAs (or antisense DNAs) or modified nucleic acids thereof.

The antisense RNA (or antisense DNA) is a single-stranded nucleic acid targeting lncRNA, which is a transcription product of the TUG1 gene. The siRNA targeting the lncRNA degrades lncRNA, while the antisense RNA (or antisense DNA) suppresses or inhibits the functions of the lncRNA. In order to enhance in vivo stability, the antisense RNA or antisense DNA is preferably a modified derivative comprising the RNA/DNA chimera structure and/or one or more modified nucleotides as described above. Specific examples of the modified nucleotides are provided above, and a further preferable example thereof is a combination of phosphorothioate modification with 2'-MOE nucleotide, 2'-OMe nucleotide, or LNA-modified nucleotide. The antisense RNA (or antisense DNA) or a modified derivative thereof is generally 12 to 100 nucleotides, preferably 15 to 50 nucleotides, more preferably 20 to 30 nucleotides, in its length. While the antisense RNA (or antisense DNA) may be more than 100 nucleotides, such a long sequence is disadvantageous in terms of, in particular, production costs. Accordingly, the nucleotide length as described above is appropriate. The antisense RNA or antisense DNA sequence can be obtained by selecting the aforementioned size of continuous nucleotides from: the nucleotide sequence of the transcript lncRNA of the TUG1 gene or the nucleotide sequence of DNA encoding the lncRNA, such as the nucleotide sequence from human TUG1 of SEQ ID NO: 1, 2, or 3; or a nucleotide sequence of a TUG1 gene that is a naturally occurring variant consisting of a nucleotide sequence having 70% or higher, 80% or higher, or 90% or higher, preferably 95% or higher, more preferably 98% or higher or 99% or higher sequence identity to each of the nucleotide sequences described above, and making a nucleotide sequence complementary to the selected nucleotide sequence or a modified nucleotide sequence thereof. The target is preferably a region of the nucleotide numbers 1044 to 1062, 1044 to 1062, or 1044 to 1062 (which is the region of #1 in FIG. 2) and/or a region of the nucleotide numbers 2997 to 5181, 2941 to 5111, or 2941 to 5125 (which is the region of #5 to #4 in FIG. 2) in the nucleotide sequence of the transcript RNA of the human TUG1 gene, such as the nucleotide sequence of SEQ ID NO: 1, 2 or 3, as described above. Specific examples of antisense RNAs each comprising at least 2, preferably 3 or 4 LNA-modified nucleotides at each end include antisense RNAs comprising the nucleotide sequences (SEQ ID NO: 28 to 35) of the antisense strands shown in FIG. 3A. Examples thereof include, but are not limited to, antisense RNAs each comprising the nucleotide sequence of any of SEQ ID NOs: 36 to 38 and 51 to 53 and the like. In the specific example, the antisense DNA comprises a nucleotide sequence derived from the sequence of the antisense RNA described above by substitution of uracil (U) with thymine (T).

2. Composition for Treatment or Prevention of Tumors

The composition of the present invention comprises, as an active ingredient, a nucleic acid that inhibits high expression of the TUG1 gene in tumor stem cells, thereby inhibiting the tumor growth. Since the composition of the present invention targets tumor stem cells, tumor regression can be achieved, and tumor metastasis can be suppressed.

The nucleic acid may be prepared in the form of a composition comprising the nucleic acid admixtured with a carrier or the like. Alternatively, the nucleic acid may be prepared such that it is incorporated into a delivery system.

A dose of the nucleic acid is, for example, about 0.01 mg to about 1,000 mg in terms of siRNA molecules per 1 kg of the body weight of a human adult, although the dose is not limited thereto. In general, a dose or a dosage should be determined by taking sexuality, age, body weight, symptoms, severity, side effects, and other factors concerning a subject into consideration. Administration can be carried out at intervals of, for example, 1 week, 2 weeks, 3 weeks, or 4 weeks. If necessary, administration can be carried out at intervals of more than 1 month.

The pharmaceutical composition can be prepared by admixing a carrier or diluent and additives, in addition to a nucleic acid as an active ingredient. Where needed, the pharmaceutical composition can be combined with another anti-cancer agent (e.g., a chemotherapeutic agent or an antibody drug) and/or other agents associated with the treatment, so as to prepare a so-called pharmaceutical kit.

The carrier or diluent can be adequately selected in accordance with the form of a pharmaceutical preparation, for example, solid preparation, semi-solid preparation, or liquid (or solution) preparation, or a dosage form (or a form of administration). Examples of dosage forms include oral preparations, such as tablets, capsules, granules, powders, syrups, and gel agents, and parenteral preparations, such as injections, drops, transmucosal agents (e.g., transnasal agents), percutaneous agents, liposomes, transrectal agents (or suppositories), inhalants, ointments, and lotions.

The diluents for liquid preparation include, for example, distilled water, sterilized water. Ringer's solution, and physiological saline, in the case of aqueous solvents. Where needed, ethanol may be mixed at an adequate amount with the aqueous solvent. In the case of liposome preparations, preparations slightly soluble in water, or the like, an organic solvent alone or a mixture of organic solvent and water may be used as the carrier or excipient. Examples of the organic solvent include ethanol, isopropanol, isobutanol, sec-butauol, tert-butanol, acetonitrile, acetone, ketone, dimethylsulfoxide, dimethylformamide, glycerol, polyethylene glycol, oil and fat such as cacao butter and soybean oil, and a combination thereof.

Examples of carriers or excipients used for solid preparations include maltose, lactose, sucrose, starch, gelatin, gum tragacanth, methylcellulose, hydroxypropyl methylcellulose, and sodium carboxymethyl cellulose.

Examples of additives include pharmaceutically acceptable excipients, thickeners, fillers, bulking agents, binders, wetting agents, disintegrating agents, lubricants, emulsifiers, dispersants, buffers, preservatives, solubilizers, antiseptic agents, flavoring agents, soothing agents, stabilizers, isotonic agents, and pH adjusting agents.

Examples of administration routes include intravenous administration, intraarterial administration, oral administration, transpulmonary administration, interstitial administration, percutaneous administration, transmucosal administration, intrarectal administration, intraperitoneal administration, and intracerebral administration. Among them, especially the preferred are intravenous administration, percutaneous administration, and transmucosal administration.

In order to protect the nucleic acid in the composition of the present invention from nucleases in vivo, the nucleic acid may be included in a liposome. As the liposome, a cationic liposome is generally used (Y. Takahashi et al., Yakugaku Zasshi, 127 (10), 1525-1531, 2007). The cationic liposome is positively charged, and it is easily bound electrostatically to the negatively-charged cell membranes. It is thus considered that a liposome complex passively bound to the cell membrane is introduced into the cytoplasm of cells via endocytosis and then it escapes from the endosome so as to be released into the cytoplasm.

The present invention also provides a method for treating a subject having a tumor that more highly expresses the TUG1 gene than in normal tissues, comprising administering the composition, as an anticancer agent, to the subject.

Examples of tumors that can be treated by the present invention include, but are not limited to, brain tumor, breast cancer, colon cancer, prostate cancer, liver cancer, lung cancer, leukemia, and lymphoma.

For example, excellent cell growth effects were observed as a result of the use of the nucleic acid in brain tumor stem cells. Accordingly, the composition comprising, as an active ingredient, the nucleic acid of the present invention has now been found to be an excellent anticancer agent targeting tumor stem cells.

The composition, the subject, the dose, the administration route, the number of administration, and other factors are as described above.

The composition of the present invention can be administered to a subject in combination with other therapeutic agents against cancer, such as chemotherapeutic agents, antibody drugs, or immune checkpoint inhibitors. The composition can be administered before, simultaneously with, or after the administration of another therapeutic agent against cancer, such as chemotherapeutic agent, antibody drug, or immune checkpoint inhibitor.

Examples of chemotherapeutic agents include, but are not limited to, anticancer agents as described in JP 2014-508515 A. Specific examples include: topoisomerase inhibitors, such as etoposide, camptothecin, topotecan, teniposide, and mitoxantrone; DNA alykylating agents, such as cisplatin, mechlorethamine, cyclophosphamide, ifosfamide, melphalan, chlorambucil, busulphan, thiotepa, carmustine, lomustine, carboplatin, dacarbazine, and procarbazine; DNA strand break-inducing agents, such as bleomycin, doxorubicin, daunorubicin, idarubicin, and mitomycin C; antimicrotubule agents, such as vincristine and vinblastine; antimetabolites, such as cytarabine, methotrexate, hydroxyurea, 5-fluorouracil, floxuridine, 6-thioguanine, 6-mercaptopurine, fludarabine, pentostatin, and chlorodeoxyadenosine; anthracycline, vinca alkaloid, epipodophyllotoxin, and temozolomide.

Examples of antibody drugs include, but are not limited to, various commercially available antibodies and antibodies to be developed and launched, such as trastuzumab and bevacizumab.

The immune checkpoint inhibitor is intended to prevent that cancer cells avoid an attack from immune cells, so as to recover the aggressiveness that the immune cells originally have against cancer cells. Examples thereof include anti-PD-1 antibodies (PD-1: programmed cell death-1) and anti-PD-L1 antibodies (PP-L1: programmed death-ligand 1), such as nivolumab and atezolizumab.

An adequate dose of the drugs is determined by taking sexuality, age, body weight, symptoms, severity, side effects, and other factors concerning a subject into consideration. Alternatively, a close level that is actually employed in clinical settings should be selected.

EXAMPLES

The present invention is described in more detail with reference to the following examples, although the technical scope of the present invention is not limited to these examples.

Example 1

<TUG1 Expression Level in Various Tumor Cell Lines>

TUG1 expression levels in various tumor cell lines were assayed using quantitative RT-PCR. As the tumor cell lines, glioma stem cell lines (GSC), glioma cell lines (T98, U251, SK-MG1, and AO2), breast cancer cell lines (MCF7, MDA231, SK-BR3, and T47D), colon cancer cell lines (Lovo, Caco-2, RKO, SW48, SW480, and SW1083), prostate cancer cell lines (PC3, LNCap, and Vcap), liver cancer cell lines (HepG2, Huh7, and A549), lung cancer cell lines (H920 and PC9), leukemia cell line (Jurkat), Burkitt's lymphoma cell line (Raji), and lymphoma cell line (Pfeiffer) were used.

The results are shown in FIG. 1 as the relative TUG1 expression ratio relative to the internal standard GAPDH (i.e., glyceraldehyde 3-phosphate dehydrogenase). The TUG1 gene expression levels in many tumor cell lines were found to be higher than the TUG1 expression levels in normal tissues (TUG1/GAPDH=0.05394 (the average of 3 normal brain tissue samples)).

Example 2

<Position of TUG1 Target Sequence and Inhibitory Effects by siRNA>

In order to design nucleic acids that inhibit the TUG I expression (i.e., siRNAs), candidate target sequence regions were selected from the full-length regions of the nucleotide sequences of TUG1 lncRNA (NR_110492 (SEQ ID NO: 1), NR_110493 (SEQ ID NO: 2) and NR_002323 (SEQ ID NO: 3)) (A. M. Khalil et al., PNAS, 106: 11667-11672, 2009, siDirect version 2.0), and siRNAs corresponding to the selected regions (i.e., si-TUG1#1 to si-TUG 1#14, where the sequences each comprise 2 deoxyribonucleotide sequences at the 3' end) were prepared by Hokkaido System Science Co., Ltd. (Sapporo, Japan) on request (FIG. 3).

Figure 2:
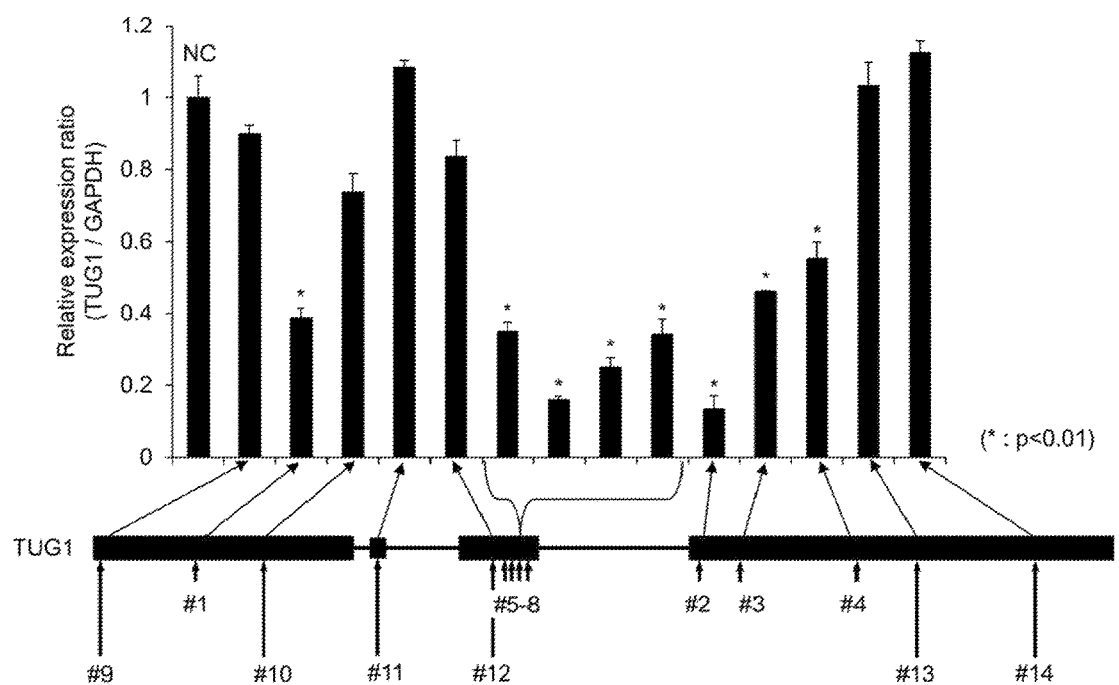
FIG. 2 shows the positions of siRNA targeting sequences for TUG1 and the growth inhibitory effects on the glioma stem cell line GSC. In the figure, si-TUG1#1 to si-TUG1#14 (their nucleotide sequences, see FIG. 3) represent the prepared modified siRNAs (i.e., RNA/DNA chimeras, wherein "dCdA" and the like at the 3' ends of the sense strand and the antisense strand are DNA sequences) and target positions in the TUG1 sequence. The inhibitory effects are represented by the relative expression ratio of TUG1/GAPDH (internal standard) relative to control siRNA ("NC"; Silencer Select Negative Control #1 siRNA (Catalog No., 4390843, Life Technologies)). The symbol "*" represents a statistical significance of $p<0.01$.
Figure 4:
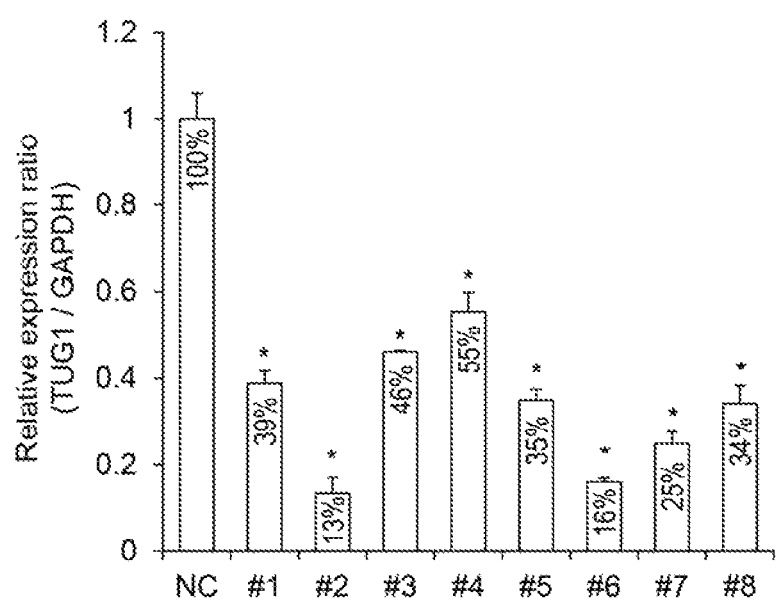
FIG. 4 shows the evaluated results of inhibitory effects on TUG1 expression in the glioma stem cell line GSC by using si-TUG1#1 to si-TUG1#8 (indicated as "#1" to "#8"). The relative TUG1 expression levels (TUG1/GAPDH (internal standard)) relative to control siRNA ("NC": Silencer Select Negative Control #1 siRNA, Catalog No. 4390843, Life Technologies) 3 days after the introduction of each modified siRNA are shown. The symbol "*" indicates statistical significance of $p<0.01$.

Various types of siRNAs were each introduced into the glioma stem cell line (GSC) (1.0×10$^5$ cells) to the final concentration of 30 nM using Lipofectamine3000 (Life Technologies) in accordance with the instructions. As control siRNA ("NC"), Silencer Select Negative Control #1 siRNA (Catalog No. 4390843, Life Technologies) was used. The TUG1 expression levels relative to the control siRNA were quantified using the GAPDH as the internal standard by means of quantitative RT-PCR (Applied BioSystems) 3 days after the introduction of siRNAs. As a result, significant inhibitory effects on TUG1 expression were observed for 8 types of siRNAs (si-TUG1#1 to si-TUG1#8) (FIG. 2 and FIG. 4). Concerning si-TUG1#9 to si-TUG1#14, however, sufficient inhibitor effects on TUG1 expression were not observed.

On the basis of the results attained above, a region of the nucleotide numbers 1044 to 1062, 1044 to 1062, or 1044 to 1062 (which is the region of #1 in FIG. 2) and/or a region of the nucleotide numbers 2997 to 5181, 2941 to 5111, or 2941 to 5125 (which is the region of #5 to #4 in FIG. 2) in the nucleotide sequence of SEQ ID NO: 1, 2 or 3 were found to be preferable as TUG1 target regions.

Example 3

<GSC Tumor Growth Inhibition>

Figure 5:
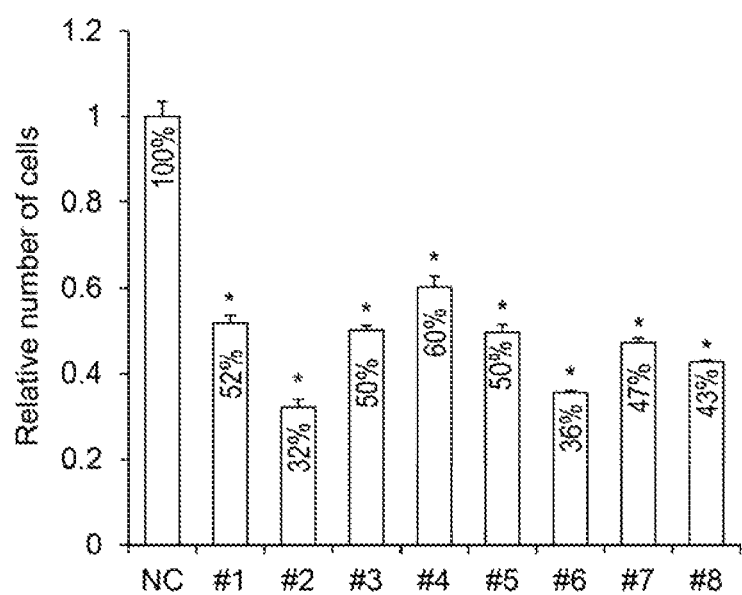
FIG. 5 shows the evaluated results of the anti-growth effects on the glioma stem cell line GSC by using si-TUG1#1 to si-TUG1#8 (indicated as "#1" to "#8"). The relative number of living GSC cells relative to control siRNA ("NC") 3 days after the introduction of each modified siRNA is shown. The symbol "*" indicates statistical significance of $p<0.01$.

The 8 types of siRNAs (si-TUG1#1 to si-TUG1#8) that have been prepared and verified for their inhibitory effects on TUG1 expression in Example 2 were introduced into GSC tumor cells via lipofection as described in Example 2. The number of survived cells was determined by trypan blue staining (Life Technologies) 3 days after the introduction of siRNAs, and the growth inhibitory effects relative to control siRNA ("NC") were analyzed. As a result, significant growth inhibitory effects were observed for the 8 types of siRNAs subjected to analysis (FIG. 5).

Example 4

<GSC Tumor Growth Inhibition by Using LNA-Modified Antisense RNA>

The antisense strand of si-TUG1#2 that has been found to most effectively inhibit TUG1 expression in Examples 2 and 3 (i.e., the sequence complementary to the lncRNA partial sequence of TUG1) was modified with LNA (i.e., locked nucleic acid; 2'-0,4'-C methylene bridge (—O—CH$_2$—)-modified nucleic acid), and three types of LNA-modified antisense RNAs (LNA-TUG1-1#1 (SEQ ID NO: 36), LNA-TUG1-1#2 (SEQ ID NO: 37), and LNA-TUG1-1#3 (SEQ ID NO: 38); FIG. 6) were prepared by GeneDesign, Inc. (Osaka, Japan) on request. Then, inhibitory effects on TUG1 expression were examined. Control siRNA ("NC"), si-TUG1#2, and the LNA-modified antisense RNAs were each introduced into the glioma stem cell line (GSC) via lipofection, the RNAs were recovered 3, 7, and 10 days after the introduction, and changes in TUG1 expression level were quantified with the elapse of time.

Figure 7:
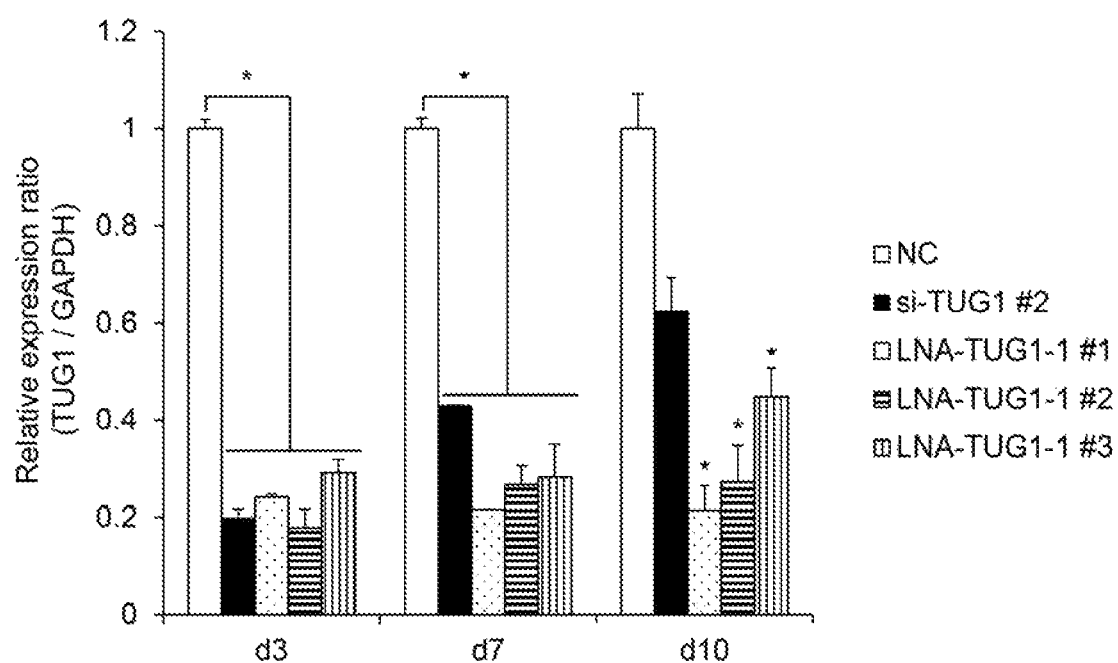
FIG. 7 shows the evaluated results of inhibitory effects on TUG1 expression by using 3 types of LNA-modified antisense RNAs (i.e., LNA-TUG1-1#1 (SEQ ID NO: 36), LNA-TUG1-1#2 (SEQ ID NO: 37), and LNA-TUG1-1#3 (SEQ ID NO: 38)) and si-TUG1#2 (sense strand: SEQ ID NO: 21; and antisense strand: SEQ ID NO: 29). si-TUG1#2 and control siRNA ("NC") were used for comparison. siRNAs and LNA-modified antisense RNAs were each introduced into the glioma stem cell line GSC, and the TUG1 expression levels relative to control siRNA ("NC") 3, 7, and 10 days after the introduction (d3, d7, and d10) are shown. The expression level is TUG1/GAPDH (internal standard). The symbol "*" indicates statistical significance of $p<0.01$.

As a result, the inhibitory effects on TUG1 expression were found to be retained for a longer period of time with the use of LNA-modified antisense RNAs than with the use of si-TUG1#2 (FIG. 7).

Figure 8:
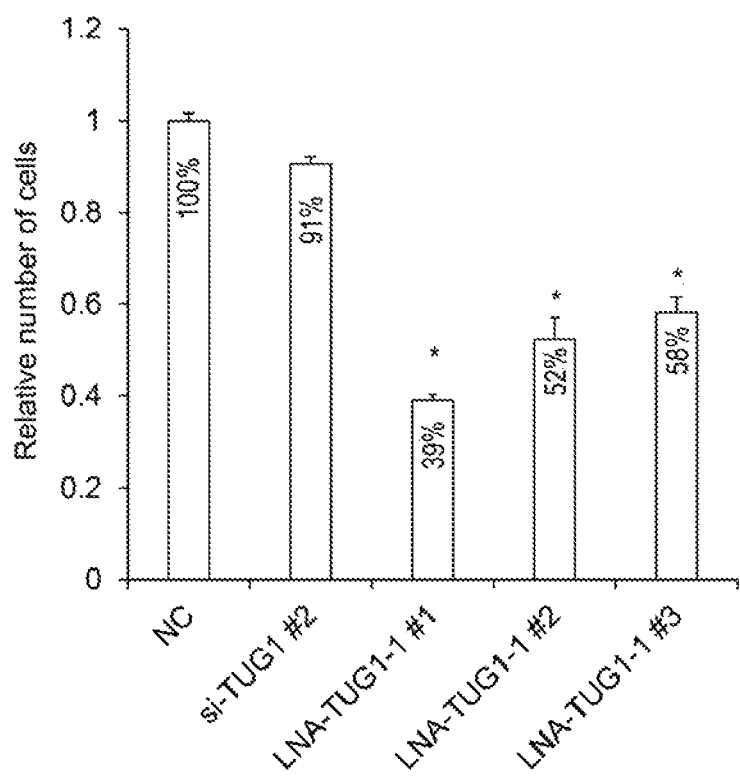
FIG. 8 shows the evaluated results of tumor cell growth inhibitory effects by using the indicated siRNAs and LNA-modified antisense RNAs (final concentration: 30 nM) on the glioma stem cell line GSC (initial number of cells: $1\times10^5$ cells). In the figure, si-TUG1#2 (sense strand: SEQ ID NO: 21; and antisense strand: SEQ ID NO: 29) and LNA-modified antisense RNAs (LNA-TUG1-1#1 (SEQ ID NO: 36), LNA-TUG1-1#2 (SEQ ID NO: 37), and LNA-TUG1-1#3 (SEQ ID NO: 38)) were each introduced into GSCs, and the relative number of living GSC cells relative to control siRNA ("NC") 10 days after the introduction are shown. The symbol "*" indicates statistical significance of $p<0.01$.

In addition, the relative number of living GSC cells was determined 10 days after the introduction of each of the siRNAs and LNA-modified antisense RNAs. As a result, significant growth inhibitory effects were observed exclusively on the LNA-modified antisense RNAs (FIG. 8).

Also, the antisense strand sequence of si-TUG1#6 (i.e., the sequence complementary to the lncRNA partial sequence of TUG1) was modified with LNA, and three types of LNA-modified antisense RNAs (LNA-TUG1-2#1 (SEQ ID NO: 51), LNA-TUG1-2#2 (SEQ ID NO: 52), and LNA-TUG1-2#3 (SEQ ID NO: 53); FIG. 9) were prepared by GeneDesign, Inc. on request. Then, inhibitory effects on TUG1 expression were examined. Control siRNA ("NC"), si-TUG1#6, and the LNA-modified antisense RNAs were each introduced into the glioma stem cell line (GSC) via lipofection, the RNAs were recovered 3, 7, and 10 days after the introduction, and changes in TUG1 expression levels were quantified with the elapse of time.

Figure 10:
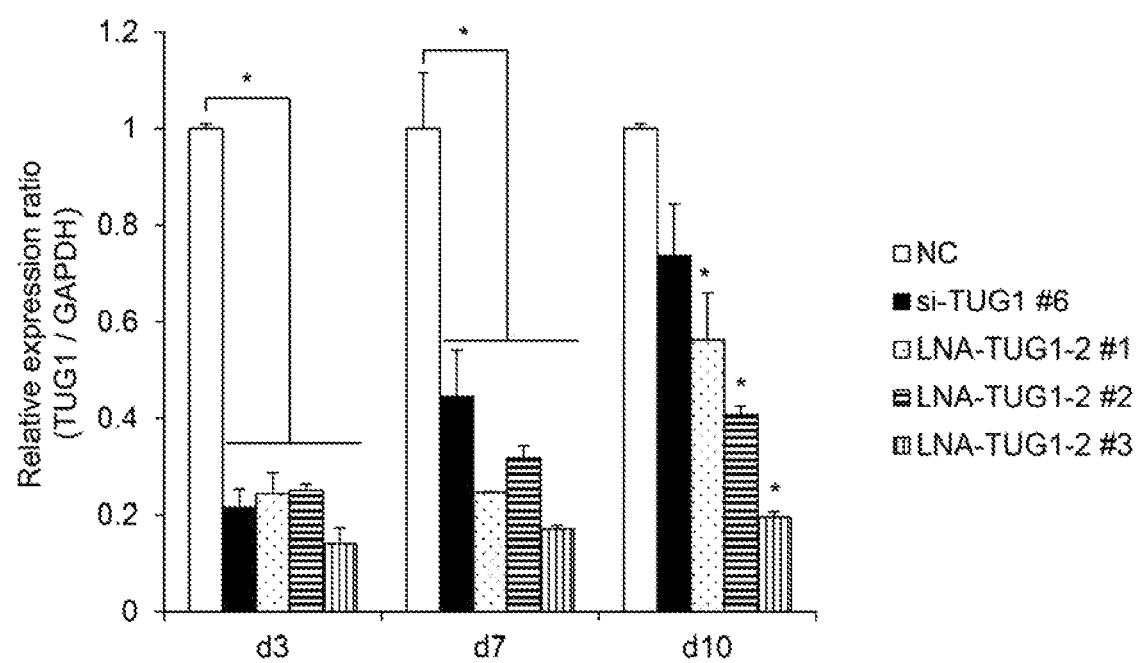
FIG. 10 shows the evaluated results of inhibitory effects on TUG1 expression by using 3 types of LNA-modified antisense RNAs (i.e., LNA-TUG1-2#1 (SEQ ID NO: 51), LNA-TUG1-2#2 (SEQ ID NO: 52), and LNA-TUG1-2#3 (SEQ ID NO: 53)) and si-TUG1#6 (sense strand: SEQ ID NO: 25; and antisense strand: SEQ ID NO: 33). si-TUG1#6 and control siRNA ("NC") were used for comparison. In the figure, siRNAs and LNA-modified antisense RNAs were each introduced into the glioma stem cell line GSC, and the relative TUG1 expression levels relative to control siRNA ("NC") 3, 7, and 10 days after the introduction (d3, d7, and d10) are shown. The expression level is TUG1/GAPDK (internal standard). The symbol "*" indicates statistical significance of $p<0.01$.

As a result, the inhibitory effects on TUG1 expression were found to be retained for a longer period of time with the use of LNA-modified antisense RNAs than with the use of si-TUG1#6 (FIG. 10).

Figure 11:
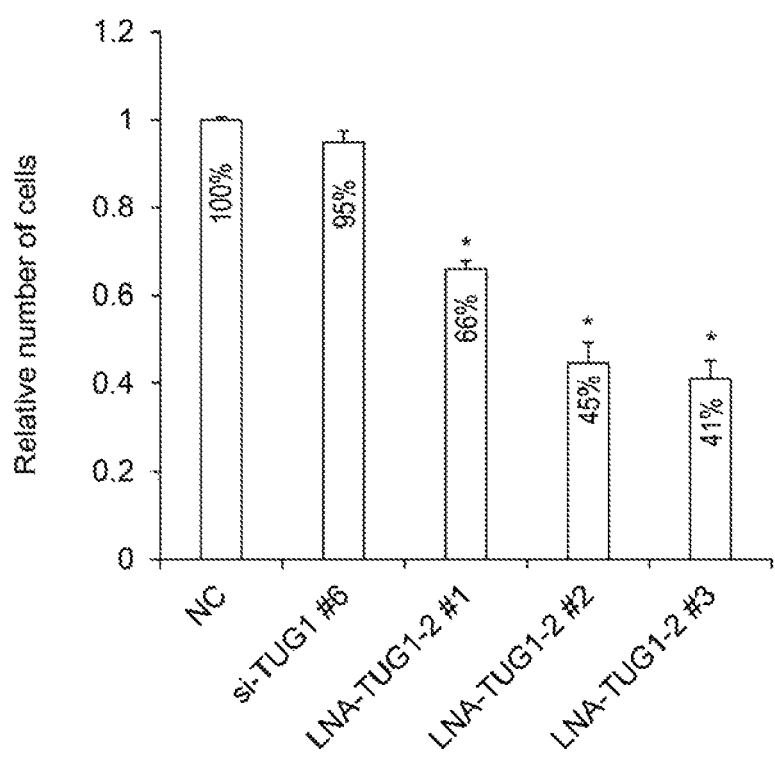
FIG. 11 shows the evaluated results of tumor cell growth inhibitory effects by using each of the indicated siRNAs and LNA-modified antisense RNAs (final concentration: 30 nM) on the glioma stem cell line GSC (initial number of cells: $1\times10^5$ cells). In the figure, si-TUG1-2#6 (sense strand: SEQ ID NO: 25; and antisense strand: SEQ ID NO: 33) and LNA-modified antisense RNAs (LNA-TUG1-2#1 (SEQ ID NO: 51), LNA-TUG1-2#2 (SEQ ID NO: 52), and LNA-TUG1-2#3 (SEQ ID NO: 53)) were each introduced into GSCs, and the relative number of living GSC cells relative to control siRNA ("NC") 10 days after the introduction is shown. The symbol "*" indicates statistical significance of p<0.01.

In addition, the relative number of living GSC cells was determined 10 days after the introduction of each of the siRNAs and LNA-modified antisense RNAs. As a result, more significant growth inhibitory effects were observed exclusively on the LNA-modified antisense RNAs, and excellent growth inhibitory effects were observed on LNA-TUG1-2#2 (SEQ ID NO: 52) and LNA-TUG-2#3 (SEQ ID NO: 53) (FIG. 11).

Example 5

<Prostate Cancer Growth Inhibition>

In the same manner as in Examples 2 and 3, si-TUG1#2 was introduced into the prostate cancer cell line PC3 via lipofection. The TUG1 expression level and the relative cell growth rate of the PC3 cell line in the prostate cancer cell line PC3 3 days after the introduction were determined in the same manner as in the examples above. As a negative control, control siRNA ("NC") was used, and the expression level was also shown as the relative TUG1 expression ratio relative to the internal standard GAPDH.

Figure 12:
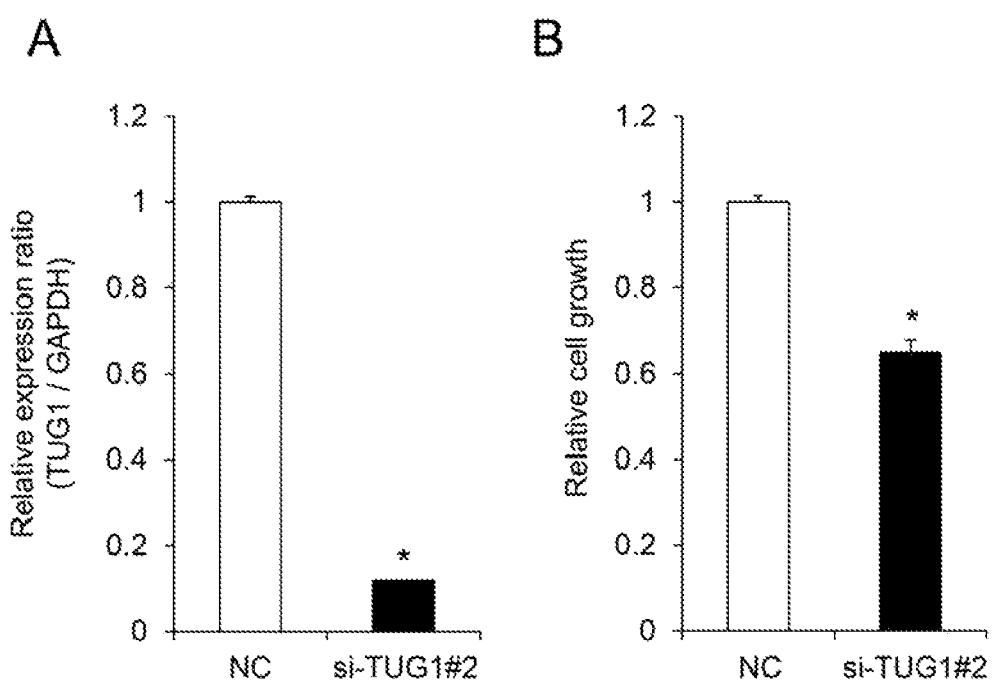
FIG. 12 shows the growth inhibitory effects on the prostate cancer cell line PC3 by TUG1 inhibition.

As a result, the growth inhibitory effects on the prostate cancer cell line PC3 induced by TUG1 inhibition were observed (FIG. 12A and FIG. 12B).

Example 6

<Tumor Growth Inhibition in GSC-Tumor-Carrying Mice>

The glioma stem cell line (GSC) was percutaneously transplanted into nude mice. The day on which the tumor size reached about 100 mm³ was designated as Day 0, LNA-TUG1-1#1 (SEQ ID NO: 36) was directly administered in an amount of 5 µg per tumor every 3 days, and the tumor size was measured up to Day 35. Control siRNA ("NC") was also administered to mice.

Figure 13:
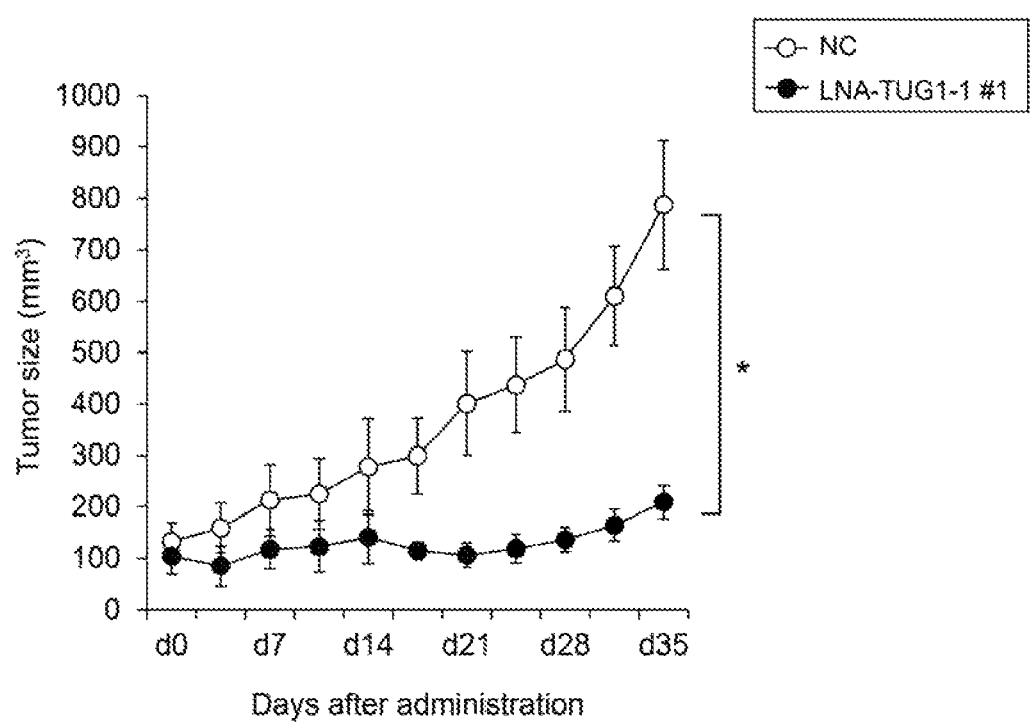
FIG. 13 shows changes in tumor size over the indicated days attained by percutaneously transplanting the glioma stem cell line GSC to nude mice and administering LNA-TUG1-1#1 (SEQ ID NO: 36) or control siRNA ("NC") intravenously to the mice every 3 days for treatment. The symbol "*" indicates statistical significance of p<0.01.

As a result, GSC growth inhibitory effects by LNA-TUG-1#1 were observed, as shown in FIG. 13.

INDUSTRIAL APPLICABILITY

According to the present invention, modified siRNAs and modified antisense RNAs that effectively inhibit TUG1 expression in particular types of tumor cells were prepared, and nucleic acids that inhibit TUG1 expression and inhibit the growth of tumor and/or tumor stem cells, such as glioma, were found. Specifically, it was confirmed that the use of LNA-modified antisense RNAs enables inhibition of TUG1 expression in tumors for a longer period of time and inhibition of the growth of tumors and/or tumor stem cells to a significant extent. According to the present invention, it was suggested that the TUG1-targeting nucleic acid drugs are effective for treatment of GBM.

SEQUENCE LISTING FREE TEXT

SEQ ID NOs: 4 to 19: siRNAs for human TUG1;

SEQ ID NOs: 20, 21, 28, 29, 43, and 49: siRNAs for human TUG1, in which (1) . . . (17) are RNAs;

SEQ ID NOs: 22 to 27, 30 to 35, 39 to 42, 44 to 48, and 50: siRNAs for human TUG1, in which (1) . . . (19) are RNAs;

SEQ ID NO: 36: LNA-modified antisense RNA, in which (1) . . . (4) and (16) . . . (19) are locked nucleic acids;

SEQ ID NO: 37: LNA-modified antisense RNA, in which (1) . . . (3) and (17) . . . (19) are locked nucleic acids;

SEQ ID NO: 38: LNA-modified antisense RNA, in which (1) . . . (4) and (17) . . . (19) are locked nucleic acids;

SEQ ID NO: 51: LNA-modified antisense RNA, in which (1) . . . (4) and (18) . . . (21) are locked nucleic acids;

SEQ ID NO: 52: LNA-modified antisense RNA, in which (1) . . . (3) and (19) . . . (21) are locked nucleic acids; and SEQ ID NO: 53: LNA-modified antisense RNA, in which (1) . . . (4) and (19) . . . (21) are locked nucleic acids.

All publications, patents, and patent applications cited herein are incorporated herein by reference in their entirety.

The invention claimed is:

1. A method for treatment of a subject having a brain tumor having a higher TUG1 gene expression as compared to normal tissues, comprising administering to the subject a composition comprising a modified antisense oligonucleotide that targets a nucleotide sequence of nucleotide numbers 3015 to 3035, or 3394 to 3412 of the nucleotide sequence of SEQ ID NO: 3, wherein the modified antisense oligonucleotide comprises a modification(s) of at least two nucleotides selected from the group consisting of: 2'-O,4'-C methylene bridge; 2'-O,4'-C ethylene bridge; 2'-methoxyethoxy; 2'-methoxy; 2'-fluoro; and a combination thereof, in a nucleotide sequence complementary to the nucleotide sequence of the nucleotide numbers 3015 to 3035, or 3394 to 3412 of SEQ ID NO: 3, wherein the modified antisense oligonucleotide comprises RNA, DNA, or a combination thereof.

2. The method of claim 1, wherein the brain tumor is glioblastoma (GBM).

3. The method of claim 1, wherein the modified antisense oligonucleotide comprises two or more modified nucleotides and two or more deoxyribonucleotides.

4. The method of claim 1, wherein the modified antisense oligonucleotide comprises two to four LNA-modified nucleotides that have a 2'-O,4'-C methylene bridge or 2'-O, 4'-C ethylene bridge at each end of the 5'- and 3'-ends.

5. The method of claim 1, wherein the modified antisense oligonucleotide comprises the nucleotide sequence of any of SEQ ID NOs: 36 to 38 and 51 to 53, or the nucleotide sequence thereof wherein uracil (u) is substituted with thymine (t).

6. The method of claim 1, wherein the modified antisense oligonucleotide further comprises a substitution of phosphodiester linkages with phosphorothioate, phosphorodithioate, alkyl phosphonate, or phosphoramidate linkages.

7. The method of claim 3, wherein the two or more modified nucleotides comprise LNA-modified nucleotides having a 2'-O,4'-C methylene bridge or 2'-O,4'-C ethylene bridge.

* * * * *

SEQUENCE LISTING

```
<160> NUMBER OF SEQ ID NOS: 53

<210> SEQ ID NO 1
<211> LENGTH: 7598
<212> TYPE: RNA
<213> ORGANISM: Homo sapiens

<400> SEQUENCE: 1
uccugcuuuc cugacccucu ccgccauuua aagaaacagu accgggggcg ggccgagcga      60
cgcagccggg acgguagcug cggugcggac cggaggagcc aucuugucuc gucgccgggg     120
agucaggccc cuaaaucgaa gaagcccugg cgcgcccucc cccccucccg ggucugguag     180
ggcgaaggaa cgggcgugcg gucgaucgag cgaucgguug gcggcucuuu cuccugcucu     240
ggcauccagc ucuuggggcg caggcccggc cgccgcggcg cgcgcccggu ggccguuggc     300
gcucgcgccg cgucuuucuu cucguacgca gaacucgggc ggcggccuau gcguuugcga     360
uucgacgagg agucguccgg guggucggcg gcggcgggca gcugcuccgc cccgcuccgg     420
gggaggcggc ggcggcagcg gccgcgggau uuggagcggc cggggaggcg gggguggccg     480
gggccggcuu ggaggccugg cgccacccuu cggggccugc aaggacccag uugggggggc     540 aggaggggc cggaggaugg uugguugugg gauuucuacu uugccuuuuc cuccuuaugc     600
cgccuuagug aggggcggga gcucuggcgg cagccccggg gugggagac gagcuccgga     660
```

```
gucggaagag cugggUUUUC UUCCgggCCU agCCaCCagU UggCggagUg aCCUUaggCg    720
aguCaCUCUg UaaUUUgUCU gCgCCUCagU UCCUCCUCU gCCUaUCaaU gUgUgUggg     780 uugaaaucgc uuuguaaacu auaaagcgug ggugUaCgUa aaggauggUU aUUgUUUaUa    840
aUUUUUUUUg aguuguaaga aaacuuagca guUCCCaaU CCUUgggUUU UgaaCCUggg    900
aaCCUUggaU uggaguuggg gauccccaaa cuuccgaaa uguggaau gugCggUUUg      960 ggggaaugau gggaauuugu gggaaugugc guuuagggg aaugaugauc CaUCgCUagC   1020
aaguuuucca aggggcugu gacccagaag aguuaagaau cacaauuucu ucaugcuaca   1080
gagaggaaac ugaggccuag augucauuug gGacccuuca caaccauuuu gaagcccugu  1140
uugagucccu gggauaugug agcuguuucu augcauaaug gauauucggg guuaacaaca  1200
guccccugcu uggcuucuau ucgaauccu uuucuucac caugggguc cugaagggug   1260 gcugaugcau augguacaau ggcacccagu guaaagcagc acaauuagg aguggaugug   1320 uucuguagca uccuauuuaa auaagccuau uuuauccuuu ggcccgucaa cucguuauc   1380 ugcugcuugu acggugccu guacuuucu gacucucauu gaccauauuc cacgaccaug   1440
guugucaucc auuacuugau ccuacuuuac augucuaggc ugugugguug ggugaaua    1500 ggcuucuuuu uacauggugc ugccagccca gcuaauuaau ggugcacgug gacuuuuagc  1560
aagcgggcuc acuggaagag acugaaccug gcauggaauu ccugaagaug uuggguuu    1620 uuucuuucu uaaucgaaag uuaacauugu cugaaaaguu uguuagaac acugcggaa     1680

CcuCaaaauc aguagauuug gaagugauuc aaagcuaaac uuuuccuug gcccuccuug   1740 uguucuaauu gcuugcaagu guaauacuag gaugucccaag augccaguu uugcuucuuu  1800 guuaguuguc agcugcuuuu aucaaauuuc aggccauuau ccaacaaaca cuauaaaaau  1860 guugaacaa uuggauuuca aacauuucg uuuugGuggag uggugcucac caagugguac  1920
agcccuaagc aagugaacac aaacacauuu aaguguauuu ugucugauua gauguuagcc  1980 aguauuugcua uuucauucaa aaugcugaaa aaaucaauug acuauuCCCu uuCCUaaag  2040 ggcagagaca gauaaucuca cuuccagaga aaugacuugg agaaaaaaaaa guguuggucu 2100 uuuugcucuu uuuguaauuaa auccggaugu accucaaaag acuuaagacu uggguGauaa 2160
gaugcuuuCC UCagcagaaa ggagggaaaa aaaacaacug gaacucaaag cuugaaauuc 2220
uguggcaaaa caugaugau ccaggauugg agguugaaaa gauuucacua cagguuucug  2280
caauaguugg agcagauaac uuucagugua gccacagcca uggacuccag auuccagau  2340 uuucaagacc uggaccugga acccgaaaga gcugucaCg augcggcagg aacacuggag  2400
guagauuuuu uuuuauuuuu gaauuuuggg acuugacc uugcugugag aaaagagaca   2460
acgacugagc aagcacuacc accagcacug uuacugggaa uuagaagacc ugaguuucug  2520
uccagacccu cagugcaaac ugaggaugcu ccauccaaag ugaauuauga uagcagacuc  2580
cuugaaagca gguccuugu uuagugcauc uuugcccaca uacaccacaa cauaucaaga  2640
ugcauuuauu aggaaggagg aguuuagaga gcaggcuauc agaauaacca cucaccuaca  2700
gaccugguac cuggauuuuu gcccgagaug auuccuacca ccuuacuacu gacgaagaca  2760
cccauuccag uggaccacug ugacccagga ggcauucagc caucaugaug uggccuuuac  2820
cuccacuccu gucuuguucu acccagauuc agcacagccc uuuauaguga agucagaguc  2880
cucaagccaa auagcuaaag cuguuuuauc acaacaaagg ccuaguuugu uccaugagug  2940
ugcauuuCaU uucuucaguu aaagCCUUca gagacacaca auaaauuugg accaggggau  3000

UUUUUaguua uuaaugcucu cugaagaaag gcaacaucuu uuugagagca gcauuggacc  3060
```

-continued

```
acaccccaca aucucaaaug auugaaauuc augaacaucu aggaucccgu gaaggucacu    3120
ggacccuguu uuuucuacuu caaauccugu aguagccuac ugaaugagaa aacauauucu    3180
gacccauugg gaucaaauca aaggcacagu gaacuccuca uagcaucuuc uuuggaauua    3240
cucaggaacc agaacuuuuu acacaaaugu aagaaauucu accaaggagu ccccuuaccu    3300
aacagcaucu cacaaggcug caccagauuc cagaaaaggc uucucuugau acaucaaggu    3360
agaaccucua ugcauuuugu gaccgacuua uucuuagauc auugguuuuc caaaggcuuu    3420
guggccauga agcccuuuga gugaaaacug ugcagaagcc cagaguaaaa gugaagcugc    3480
ucuggaugaa guagugaagc aagaguaggg gccugaaucc ugcuacaacu aucuuccuuu    3540
accaccgugg ugacaccuaa ggggacuucc uuacaacacc uugaacucuu ccgaacacag    3600
uuugaaaacc acugccccag acagcaauau guuugaccug aauggcauuc caaucuuuuc    3660
uguaccucca cucagcacag uucauguuca guagaugcug aacauucuua gaaauacugu    3720
gugugaacuu agaaaagugc aagaagacag gcaugucuuu gaccccagga augaucauuu    3780
gcugaagaug gugucaagug aaccuagauu aacagcccuc cacuccagau ggauauccag    3840
ugauuccuag aaugggauau agccagagaa caauucuaug cacccuacac ugacagacuc    3900
ccuuaagcaa caccagaugc ucuacuggua cuugaaguac augacuuuga agucuugacc    3960
cuccaugaau accgaauua ucagcaagcg gguuuugaag cuggugccuc auugaggcca    4020
uauuagagca acuuguacau uugaccucuu guuaucagcc augguacucu acuucgugug    4080
caagagauaa cuaugaaagc caaauucaaa uacuggcaac auuuccuaaa ggggucaau     4140 aucuaucauu cgucuucuuu uccaaacuac acaucacugu augacucaac caguagcagu    4200
uauauugccc cuugguuuuu auucaguuua acuacuguuu ccaagauaaa ugagcuaaua    4260
agcuuuaaaa aaaaaaaaaa aaaaggcuga auucuuuuuu cuucaucacu ggcauaucug    4320
ccuauucucc agaauuauua ugacuauuca gcucacuuua acaguugaac uucaagcgac    4380
aaucuuugaa cacccccuucu caugugauuu aaaaugaaac cauuuggaaa aguuucuucu    4440
agccaguaau agauuuuuuu uuuauuugcu cugccuugug ccgagagaug uucuuuuaag    4500
augaaucuuu ugaugucuga uaccaccaaa uauaggugu agggagaguu ggaggcuggc     4560
ccuuugagca ggccauuagc uuacuugcug ggcauuccg auagcuuauu gccuaccuuu    4620
uugcuggaaa caaacugauu ugaaaacaa aucuaugaa gacugcagcu aaggauuuua     4680
ucgguagacu uaagagcuuu ugccuugug gauauuuag uggaaccaca ucagucucaa     4740 uacgucauu uuacacugac ucagagcagc ugacuucauu ccuugccaug auauauauuu     4800
aaggcaggca uguaacaga cauaaagaca acuuaucugu uucagcagga aggauucagu    4860
uuaugaacuc ucagaccaga ucauguugaa caaggagacu ugaugugug caugagaaa      4920 acucauucuu uacuucccag ucaauuuaaa ggccagcuau ccugagcuac ucgaaugaau    4980
gcacugguua acauuggaa auaguuugu uauauccuug ucucucucua ggccaauugu     5040
gauuacauga cucgacucua caucucguca aacaaggccu aggucugguu gcuguagacu    5100
gcucgcccuc aacaaauaaa aucgguuga cuagccuccu uguauauaca acuauuauuu    5160
guuaagaaga aauuaucguc aauuucuac uaccuuccaa uugucagcuc uuuuuuuccu    5220
cucugguuuu uccauacuu uacagaaaaa gacauugauc uauacugcca uucccucuaa    5280
uccugccaua cucagucaaa aggaaugacu uaagaugaag augaucaucu gcucgagucu    5340 aaauauaca uuguauauaa gaauuggua uuagaaaagc aaaaaaccua aaacuuaaau      5400
```

| | |
|---|---|
| cuaggagucu guauacuguc uccaugucuc caugccucag aucucaucua aaucuuugaa | 5460 |
| cagcaccauu caaccaaucu gaggccuuga cuugcuugua agaugauucu cagagaucgg | 5520 |
| cugaguuaaa aaagaugacg acuugauuac caaagaaagu agggccaacu uugacaaauc | 5580 |
| uggcucugcu gacccuguca cucccagaug uagcauagac uccuaaacag aaccucaagu | 5640 |
| cugauugagg auaaggccuu cuccugagcu gaaaguucuu uggcagauga gcaagaaacu | 5700 |
| gaaagcugau guaccugacu ggcucuguaa gaucagaaaa cuguauccag aauaagcccu | 5760 |
| auggauuaac cccugaguac ccagaguaaa aacuaauuua cagaacuucc uuauugaucu | 5820 |
| gcugguucuu ccagaucaua uucuggcuau ugguauggcu ggccuuucug aagguacccu | 5880 |
| gcuugucuau uuccugacu cagcucuugc cugccuuuuu cacauguugc ugcaauuaga | 5940 |
| cucaccguga ggacuacagu caauuucagu cuaucuugug cccaauacaa caaggauuuu | 6000 |
| uaauaguaac aacccacacc ucacccacua ggacucaaug uucacaacag gaaggaccau | 6060 |
| ugcugcauac uccuugacca gcaacuuuuu ugaagauauu uuuaagugca gaguaggccu | 6120 |
| cuauccugu auguaauugu ucauuuucag caccuggaac cucaucuauc gggucuggaa | 6180 |
| ggaauacagc aguucgaaag ccgcguccau uucucuccuu caguagugca gaaaugaguc | 6240 |
| cgauuccacca guacacacag aacguaccauc guucaaccua gcaaagaag aaaaguuucc | 6300 |
| acuguacuua aaauuuacag cugacucaaa ugccucaca gaauuauuug auguagaagg | 6360 |
| cuaguugucu uacuucagau cagcaggaca guugggcucu cagacucaug accacgagu | 6420 |
| uugcuugugu ugaaacugug guuucaucca acauaugcua uuggacauga uuauuauucc | 6480 |
| auucaaaugg auuacagacu ucuugaggac aggacaaacu uaucucucau gguguuuuu | 6540 |
| uagaauacuu uuauaaccaa ggaagaaacc augccagcug uuaccauuca acuucuuaag | 6600 |
| cagagauuaa gcuuuucau aucguucuu uccuggaca ucaguaguuu uuaauugccc | 6660 |
| agcauccguu ccaucuugua acaaucccu gauguucuu aaaaccaccu cuuccuauuu | 6720 |
| ucagucugug guuggacag ucugacccaa ccuugagcuu ugugggugaa cauguaauuc | 6780 |
| agaccucauc aaucagcaaa uccaucugaa cuguggagga gaagcucucu uuacugaggg | 6840 |
| ugcuuuagcu uuguaggaug aaaaccucaa acuaacaggg ccuaccaugu agagaaugaa | 6900 |
| gccagugcag gggaaagcag agccaaaaua uggagagacu ugaauccuga ugacagcguu | 6960 |
| ugugccccug gauccaaccg ugccugaagc uagaauaucc ccuggacuuu ucaguuaugu | 7020 |
| gaaccaauaa auacccuuuu uugcuuaagu acuuugagu ugggguucug uuacuugaaa | 7080 |
| uugaauccac acuaauauau cuaccaacau ugagacuuga cagauccaag uauuuauuaa | 7140 |
| gcuagagguc auggucacug aaauuacuuu ccaagugga agacaaaaug aaacaggaac | 7200 |
| ugagggaaua uuuaagaucc cacagaagcg uaaaaaugac auguuagaaa guaauagaaa | 7260 |
| accuaaaugu cugucauuaa aggauagguu aaggugugu ucagccauau aggaauaucu | 7320 |
| cguaucuguu aaaaugaaua aaguacauuc auugugauaug gaaaaauggc caugauacau | 7380 |
| uaggugaaac aaguuauuaa uagaaaagug uacaguguga acucauuuua aaaugugugu | 7440 |
| gcuuauguuu auaaaugcau agaaaggucu auucacagcu uucuuugaac aguguagauc | 7500 |
| acaugaaacu uucaacuuua uacauuucug uauuaauauu uuacacuacc cacauuauuu | 7560 |
| uuaaacuuua uuuuaaauaa agaauuuuua aaauuaaa | 7598 |

<210> SEQ ID NO 2
<211> LENGTH: 7528
<212> TYPE: RNA
<213> ORGANISM: Homo sapiens

<400> SEQUENCE: 2

```
uccugcuuuc cugacccucu ccgccauuua aagaaacagu accggggcg ggccgagcga      60
cgcagccggg acguagcug cggugcggac cggaggagcc aucuugucuc gucgccgggg     120
agucaggccc cuaaaucgaa gaagcccugg cgcgcccucc cccccucccg ggucugguag    180
ggcgaaggaa cgggcgugcg gucgaucgag cgaucgguug gcggcucuuu cuccugcucu    240
ggcauccagc ucuuggggcg caggcccggc cgccgcggcg cgcgcccggu ggccguuggc    300
gcucgcgccg cgucuuucuu cucguacgca gaacucgggc ggcggccuau gcguuugcga    360
uucgacgagg agucguccgg gguggucgcg gcggcgggca gcugccccgc cccgcuccgg    420
gggaggcggc ggcggcagcg gccgcgggau uggagcggc cggggaggcg gggguggccg    480
gggccggcuu ggaggccugg cgccacccuu cggggccugc aaggaccag uugggggggc     540
aggaggggc cggaggaugg uugguugugg gauuucuacu uugccuuuuc cuccuuaugc     600
cgccuuagug aggggcggga gcucuggcgg cagccccggg guggggagac gagcuccgga    660
gucggaagag cuggguuuuc uuccgggccu agccaccagu uggcggagug accuuaggcg    720
agucacucug uaauuugucu gcgccucagu uccuccucu gccuaucaau gugugugggg    780
uugaaaucgc uuuguaaacu auaaagcgug ggguacgua aaggauggu auuguuuaua     840
auuuuuuuug aguuguaaga aaacuuagca guuccccaau ccuuggguuu ugaaccuggg    900
aaccuuggau uggaguuggg gauccccaaa cuuccugaaa uguggggaau gugcgguuug    960
ggggaaugau gggaauuugu gggaaugugc guuuuagggg aaugaugauc caucgcuagc   1020
aaguuuucca aggggcugu gacccagaag aguuaagaau cacaauuucu ucaugcuaca    1080
gagaggaaac ugaggccuag augucauuug ggacccuuca caaccauuu gaagcccugu    1140
uugagucccu gggauaugug agcuguuucu augcauaaug gauauucggg guuaacaaca   1200
gucccccugcu uggcuucuau ucugaauccu uuucuuucac caugggguc cugaaggug    1260
gcugaugcau augguacaau ggcacccagu guaaagcagc uacaauuagg aguggaugug   1320
uucuguagca uccauuuaa auaagccuau uuuauccuuu ggcccgucaa cucuguuauc    1380
ugcugcuugu acggugccu uacuuuucu gacucucauu gaccauauuc cacgaccaug     1440
guugucaucc auuacuugau ccuacuuuac augucuaggc ugugugguug guggugaaua   1500
ggcuucuuuu uacaugugc ugccagccca gcuaauuaau ggugcacgug gacuuuagc     1560
aagcgggcuc acuggaagag acugaaccug gcauggaauu ccgaagaug uuggggguuu    1620
uuuucuuuuc uaaucgaaag uuaacauugu cugaaaaguu uuguuagaac uacgcggaa    1680
ccucaaaauc aguagauuug gaagugauuc aaagcuaaac uuuuuccuug gcccuccuug    1740
uguucuaauu gcuugcaagu guaauacuag gauguccaag augccaguuu uugcuucuuu   1800
guuaguuguc agcugcuuu aucaaauuuc aggccauuau ccaacaaaca cuauaaaaau   1860
guugaacaa uuggauuuca aacauuuucg uuuuguggag uggugcucac caaguggac    1920
agcccuaagc aagugaacac aaacacauuu aagguauuu ugucugauua gauguuagcc   1980
aguuaugcua uuucauucaa augucugaaa aaaucaauug acuauucccu uuuccuaaag   2040
ggcagagaca gauaaucuca cuuccagaga augacuugg agaaaaaaaa guguuggucu    2100
uuuugcucuu uguaauuaa auccggaugu accucaaaag acuaagacu guggugauaa    2160
gaugcuuucc ucagcagaaa ggagggaaa aaaacaacug gaacucaaag cuugaaauuc    2220
uguggcaaaa caugagaugu ccaggauugg agguugaaaa gauuucacua caguguucug   2280
```

```
caauaguugg agcagauaac uuucagugua gccacagcca uggacuccag auuccagau    2340 uuucaagacc uggaccugga acccgaaaga gcuugucacg augcggcagg aacacuggag    2400
guagauuuuu uuuuauuuuu gaauuuuggg acuguugacc uugcugugag aaaagagaca    2460
acgacugagc aagcacuacc accagcacug uuacugggaa uuagaagacc ugaguuucug    2520
uccagacccu cagugcaaac ugaggaugcu ccauccaaag ugaauuaugu ccugugccuc    2580
cugauugcug aguguucacc uggaccuucu gacuaccuuc ccugugcuau ccaucagcc     2640 uacagaccug guaccuggau uuugcccga gaugauuccu accaccuuac uacugacgaa     2700
gacacccauu ccaguggacc acugugaccc aggaggcauu cagccaucau gauguggccu    2760
uuaccuccac uccugucuug uucuacccag auucagcaca gcccuuuaua gugaagucag    2820
aguccucaag ccaaauagcu aaagcuguuu uaucacaaca aaggccuagu uguuccaug     2880 agugugcauu ucauucuuc aguuaaagcc uucagagaca cacaauaaau uuggaccagg     2940
ggauuuuuua guuauuaaug cucucugaag aaaggcaaca ucuuuuugag agcagcauug    3000
gaccacaccc cacaaucuca aaugauugaa auucaugaac aucuaggauc ccgugaaggu    3060
cacuggaccc uguuuuuucu acuucaaauc cuguaguagc cuacugaaug agaaaacaua    3120
uucugaccca uugggaucaa aucaaaggca cagugaacuc cucauagcau cuucuuugga    3180
auuacucagg aaccagaacu uuuuacacaa auguaagaaa uucuaccaag gaguccccuu    3240
accuaacagc aucucacaag gcugcaccag auuccagaaa aggcuucucu ugauacauca    3300
agcauuuugu gaccgacuua uucuuagauc auugguuuuc caaaggcuuu guggccauga    3360
agcccuuuga gugaaaacug ugcagaagcc cagaguaaaa gugaagcugc ucuggaugaa    3420
guagugaagc aagaguaggg gccugaaucc ugcuacaacu aucuuccuuu accaccgugg    3480
ugacaccuaa ggggacuucc uuacaacacc uugaacucuu ccgaacacag uuugaaaacc    3540
acugccccag acagcaauau guuugaccug aauggcauuc caaucuuuuc uguaccucca    3600
cucagcacag uucauguuca guagaugcug aacauucuua gaaauacugu gugugaacuu    3660
agaaaagugc aagaagacag gcaugucuuu gacccaggga augaucauuu gcugaagaug    3720
gugucaagug aaccuagauu aacagcccuc cacuccagau ggauauccag ugauuccuag    3780
aaugggauau agccagagaa caauucuaug cacccuacac ugacagacuc ccuuaagcaa    3840
caccagaugc ucuacuggua cuugaaguac augacuuuga agucuugacc cuccaugaau    3900
accugaauua ucagcaagcg gguuuugaag cuggugccuc auugaggcca auuagagca    3960 acuuguacau uugaccucuu guaucagcc augguacucu acuucgugug caagagauaa    4020
cuaugaaagc caaauucaaa uacuggcaac auuccuaaa ggggcucaau aucaucauu     4080 cgucuucuuu uccaaacuac acaucacugu augacucaac cagugcagu uauauugccc     4140 cuugguuuuu auucaguuua acuacuguuu ccaagauaaa ugagcuaaua agcuuuaaaa    4200
aaaaaaaaaa aaaggcuga auucuuuuu cuucaucacu ggcauaucug ccauuucucc     4260
agaauuauua ugacuauuca gcucacuuua acaguugaac uucaagcgac aaucuuugaa    4320
caccccuucu caugugauuu aaaaugaaac cauuuggaaa aguuucuucu agccaguaau    4380
agauuuuuuu uuuaauugcu cugccuugug ccgagaugau ucuuuuaag augaaucuuu      4440 ugaugucuga uaccaccaaa uauaggugu agggagagu ggaggcuggc ccuuugagca       4500
ggccauuagc uuacuugcug ggcauuuccg auagcuauu gccaccuuuu ugcuggaaa      4560 caaacugauu ugaaaacaa aaucuaugaa gacugcagcu aaggauuuua ucgguagacu     4620
uaagagcuuu ugccuugug gauauuuuag uggaaccaca ucagucucaa uacugucauu     4680
```

-continued

```
uuacacugac ucagagcagc ugacuucauu ccuugccaug auauauauuu aaggcaggca    4740
uuguaacaga cauaaagaca acuuaucugu ucagcagga aggauucagu uuaugaacuc    4800
ucagaccaga ucauguugaa caaggagacu ugaugugug ucaugagaaa acucauucuu    4860
uacuucccag ucaauuuaaa ggccagcuau ccugagcuac ucgaaugaau gcacugguua    4920
aacauuggaa auaguuuguu uauauccuug ucucucucua ggccaauugu gauuacauga    4980
cucgacucua caucucguca aacaaggccu aggucgguu gcuguagacu gcucgcccuc    5040
aacaaauaaa aucgguuga cuagccuccu uguauauaca acuauuauuu guuaagaaga    5100
aauuaucguc aauuuucuac uaccuuccaa ugucagcuc uuuuuuuccu cucugguuuu    5160
uccuauacuu uacagaaaaa gacauugauc uauacugcca uucccucuaa ccugccaua    5220 cucagucaaa aggaaugacu uaagaugaag augaucaucu gcucgagucu aaaauauaca    5280
uuguauauaa gaauuggug uuagaaaagc aaaaaaccua aaacuuaaau cuaggagucu    5340
guauacuguc uccaugcucu caugccucag aucucaucua aaucuuugaa cagcaccauu    5400
caaccaaucu gaggccuuga cuugcuugua agaugauucu cagagaucgg cugaguuaaa    5460
aaagaugacg acuugauuac caaagaaagu agggccaacu uugacaaauc uggcucugcu    5520
gacccuguca cucccagaug uagcauagac uccuaaacag aaccucaagu cugauugagg    5580
auaaggccuu cuccugagcu gaaaguucu uggcagauga gcaagaaacu gaaagcugau    5640
guaccugacu ggcucuguaa gaucagaaaa cuguauccag aauaagcccu auggauuaac    5700
cccugaguac ccagaguaaa aacuaauuua cagaacuucc uuauugaucu gcugguucuu    5760
ccagaucaua uucuggcuau ugguauggcu ggccuuucug aagguacccu gcuugucuau    5820 uuuccgacu cagcucuugc cugccuuuuu cacauguugc ugcaauuaga cucaccguga    5880
ggacuacagu caauuucagu cuacuugug cccaauacaa caaggauuuu uaauaguaac    5940
aacccacacc ucacccacua ggacucaaug uucacaacag gaaggaccau ugcugcauac    6000
uccuugacca gcaacuuuuu ugaagauauu uuuaagugca gaguaggccu cuauuccugu    6060
auguaauugu ucauuuucag caccuggaac cucaucuauc gggucuggaa ggaauacagc    6120
aguucgaaag ccgcguccau uucucuccuu caguagugca gaaaugaguc cgauucacca    6180
guacacacag aacuguacca guucaaccua gcaaaagaag aaaaguuucc acuguacuua    6240
aaauuuacag cugacucaaa uugccucaca gaauuauuug auguagaagg cuaguugucu    6300
uacuucagau cagcaggaca guugggcucu cagacucaug accacugagu uugcuugugu    6360
ugaaacugug guucaucca acauaugcua uggacauga uauuauucc auucaaaugg    6420 auuacagacu ucuugaggac aggacaaacu uaucucucau ggugguuuuu uagaauacuu    6480
uuauaaccaa ggaagaaacc augccagcug uuaccauuca acuucuuaag cagagauuaa    6540 gcuuuucau aucguucuu auccuggaca ucagaguuu uuaauugccc agcauccguu    6600
ccaucuugua acaaccccu gauguuucu aaaaccaccu cuuccuauuu ucagucugug    6660
guuuggacag ucugacccaa ccugagcuu ugugggugaa caugaauuc agaccucauc    6720 aaucagcaaa uccaucugaa cugugga ggaagcucu uuacgaggg ugcuuuagcu    6780 uuguaggaug aaaaccucaa acuaacaggg ccuaccaugu agagaaugaa gccagugcag    6840
gggaaagcag agccaaaaua uggagagacu ugaauccuga ugacagcguu ugugcccug    6900 gauccaaccg ugccugaagc uagaauaucc ccuggacuuu ucaguuaugu gaaccaauaa    6960 auacccuuu uugcuuaagu uacuuugagu uggguuucug uuacuugaaa uugaauccac    7020
```

| | |
|---|---:|
| acuaauauau cuaccaacau ugagacuuga cagauccaag uauuuauuaa gcuagagguc | 7080 |
| auggucacug aaauuacuuu ccaaagugga agacaaaaug aaacaggaac ugagggaaua | 7140 |
| uuuaagaucc cacagaagcg uaaaaaugac augguagaaa guaauagaaa accuaaaugu | 7200 |
| cugucauuaa aggauaggu uaaggugugg ucagccauau aggaauaucu cguaucuguu | 7260 |
| aaaaugaaua aaguacauuc auuguguaug gaaaaauggc caugauacau uaggugaaac | 7320 |
| aaguuauuaa uagaaaagug uacaguguga acucauuuua aaaugugugu gcuuauguuu | 7380 |
| auaaaugcau agaaaggucu auucacagcu uucuuugaac aguguagauc acaugaaacu | 7440 |
| uucaacuuua uacauuucug uauuaauauu uuacacuacc cacauuauuu uuaaacuuua | 7500 |
| uuuuaaauaa agaauuuuua aaauuaaa | 7528 |

```
<210> SEQ ID NO 3
<211> LENGTH: 7542
<212> TYPE: RNA
<213> ORGANISM: Homo sapiens

<400> SEQUENCE: 3
```

| | |
|---|---:|
| uccugcuuuc cugacccucu ccgccauuua aagaaacagu accgggggcg ggccgagcga | 60 |
| cgcagccggg acgguagcug cggugcggac cggaggagcc aucuugucuc gucgccgggg | 120 |
| agucaggccc cuaaaucgaa gaagcccugg cgcgcccucc cccccucccg ggucugguag | 180 |
| ggcgaaggaa cgggcgugcg gucgaucgag cgaucgguug gcggcucuuu cuccugcucu | 240 |
| ggcauccagc ucuuggggcg caggcccggc cgccgcggcg cgcgcccggu ggccguuggc | 300 |
| gcucgcgccg cgucuuucuu cucguacgca gaacucgggc ggcggccuau gcguuugcga | 360 |
| uucgacgagg agucguccgg guggucggcg gcggcgggca gcugcuccgc cccgcuccgg | 420 |
| gggaggcggg ggcggcagcg gccgcgggau uggagcggc cggggaggcg ggguggccg | 480 |
| gggccggcuu ggaggccugg cgccacccuu cgggccugc aaggacccag uuggggggc | 540 |
| aggaggggggc cggaggaugg uugguugugg gauuucuacu uugccuuuuc cuccuuaugc | 600 |
| cgccuuagug aggggcggga gcucuggcgg cagccccggg gugggagac gagcuccgga | 660 |
| gucggaagag cugggguuuc uuccggggccu agccaccagu uggcggagug accuuaggcg | 720 |
| agucacucug uaauuugucu gcgcucucagu uuccuccucu gccaucaau uguguggggg | 780 |
| uugaaaucgc uuuguaaacu auaaagcgug ggguacgua aaggauggu auuguuaua | 840 |
| auuuuuuug aguguaaga aaacuuagca guuccccaau ccuuggguuu ugaaccuggg | 900 |
| aaccuuggau uggaguuggg gauccccaaa cuuccugaaa uuggggaau ugcgguuug | 960 |
| ggggaaugau gggaauuugu gggaaugugc guuuagggg aaugaugauc caucgcuagc | 1020 |
| aaguuuccca aggggggcugu gacccagaag aguuaagaau cacaauuucu ucaugcuaca | 1080 |
| gagaggaaac ugaggccuag augucauuug ggacccuuca caaccauuuu gaagcccugu | 1140 |
| uugagucccu gggauaugug agcuguuucu augcauaaug gauauucggg guuaacaaca | 1200 |
| guccccugcu uggcuucuau ucugaauccu uucuuucac caugggggc cugaagggug | 1260 |
| gcugaugcau augguacaau ggcacccagu guaaagcagc uacaauuagg aguggaugug | 1320 |
| uucuguagca uccauuuaa auaagccuau uuuauccuuu ggcccgucaa cucguuauc | 1380 |
| ugcugcuugu acggugccu uacuuuucu gacucucauu gaccauauuc cacgaccaug | 1440 |
| guugucaucc auuacuugau ccuacuuuac augucuaggc uguggguug gugugaaua | 1500 |
| ggcucucuuu uacaugggc ugccagccca gcuaauuaau ggcacugug acuuuuagc | 1560 |
| aagcgggcuc acuggaagag acugaaccug gcauggaauu ccugaagaug uuuggggguu | 1620 |

```
uuuucuuucu uaaucgaaag uuaacauugu cugaaaaguu uuguuagaac uacugcggaa    1680
ccucaaaauc aguagauuug gaagugauuc aaagcuaaac uuuuuccuug gcccuccuug    1740
uguucuaauu gcuugcaagu guaauacuag gauguccaag augccaguuu ugcuucuuu    1800 guuaguuguc agcugcuuuu aucaaauuuc aggccauuau ccaacaaaca cuauaaaaau    1860
guuugaacaa uuggauuuca acauuuucg uuuuguggag uggugcucac caaguggguac    1920 agcccuaagc aagugaacac aaacacauuu aaguguauuu ugucugauua gauguuagcc    1980
aguuaugcua uuucauucaa augucugaaa aaucaauug acuauccccu uuccuaaag    2040 ggcagagaca gauaaucuca cuuccagaga aaugacuugg agaaaaaaa guuuggucu    2100 uuuugcucuu uuguaauuaa auccggaugu accucaaaag acuaagacu guggugauaa    2160 gaugcuuucc ucagcagaaa ggagggaaaa aaaacaacug gaacucaaag cuugaaauuc    2220
uguggcaaaa caugagaugu ccaggauugg agguugaaaa gauuucacua caguguucug    2280
caauaguugg agcagauaac uuucaguugua gccacagcca uggacuccag auuuccagau    2340
uuucaagacc uggaccugga acccgaaaga gcuugucacg augcggcagg aacacuggag    2400 guagauuuu uuuuuauuu uuu gaauuugg cuguugacc uugcugugag aaaagagaca    2460
acgacugagc aagcacuacc accagcacug uuacugggaa uuagaagacc ugaguuucug    2520
uccagacccu caguggcaaac ugaggaugcu ccauccaaag ugaauaugu ccugugccuc    2580 cugauugcug aguguucacc uggaccuucu gacuaccuuc ccugugcuau ccaucagcc    2640 uacagaccug guaccuggau uuugcccga gaugauuccu accaccuuac uacugacgaa    2700
gacacccauu ccaguggacc acugugaccc aggaggcauu cagccaucau gauggggccu    2760
uuaccuccac uccugucuug uucuacccag auucagcaca gcccuuuaua gugaagucag    2820
aguccucaag ccaaauagcu aaagcuguuu uaucacaaca aaggccuagu uuguuccaug    2880
agugugcauu ucauucuuc aguuaaagcc uucagagaca cacaauaaau uuggaccagg    2940 ggauuuuua guuauuaaug cucucugaag aaaggcaaca ucuuuugag agcagcauug    3000 gaccacaccc cacaaucuca aaugauugaa auucaugaac aucuaggauc ccgugaaggu    3060
cacuggaccc uguuuuucu acuucaaauc cuguaguagc cuacugaaug agaaacaua    3120 uucugaccca uugggaucaa aucaaaggca caguggaacuc cucauagcau cuucuuugga    3180
auuacucagg aaccagaacu uuuuuacaa auguaagaaa uucuaccaag gaguccccuu    3240
accuaacagc aucucacaag gcugcaccag auuccagaaa aggcuucucu ugauacauca    3300 agguagaaacc ucuaugcauu uugugaccga cuuauucuua gaucauuggu uuccaaagg    3360 cuuguggcc augaagcccu ugagugaaa acugugcaga agcccagagu aaaagugaag    3420
cugcucugga ugaaguagug aagcaagagu agggccuga auccugcuac aacuaucuuc    3480
cuuuaccacc guggugacac cuaaggggac uuccuuacaa caccuugaac ucuuccgaac    3540
acaguuugaa aaccacugcc ccagacagca auaugguuga ccugaauggc auuccaaucu    3600
uuucuguacc uccacucagc acaguucaug uucaguagau gcuaacauu cuuagaaaua    3660 cugugugugu acuugaaaa gugcaagaag acaggcaugu cuugaccccc aggaaugauc    3720
auuugcugaa gauggguuca agugaaccua gauuaacagc ccuccacucc agauggauau    3780
ccagugauuc cuagaauggg auauagccag agaacaauuc uaugcacccu acacugacag    3840
acucccuuaa gcaacaccag augcucuacu ggguacuugaa guacaugacu uugaagucuu    3900
gacccuccau gaauaccuga auuaucagca agcggguuuu gaagcugguug ccucauugag    3960
```

-continued

```
gccauauuag agcaacuugu acauuugacc ucuuguuauc agccauggua cucuacuucg    4020
ugugcaagag auaacuauga aagccaaauu caaauacugg caacauuucc uaaaggggcu    4080
caauaucuau cauucgucuu cuuuuccaaa cuacacauca cuguaugacu caaccaguag    4140
caguuauauu gccccuuggu uuuuauucag uuuaacuacu guuccaaga uaaaugagcu    4200 aauaagcuuu aaaaaaaaaa aaaaaaaagg cugaauucuu uuuucuucau cacuggcaua    4260
ucugccuauu cuccagaauu auuaugacua uucagcucac uuuaacaguu gaacuucaag    4320
cgacaaucuu ugaacacccc uucucaugug auuuaaaaug aaaccauuug gaaaaguuuc    4380
uucuagccag uaauagauuu uuuuuuuaau ugcucugccu ugugccgaga gauguucuuu    4440
uaagaugaau cuuuugaugu cugauaccac caaauauagg ugguagggag aguuggaggc    4500
uggcccuuug agcaggccau uagcuuacuu gcugggcauu uccgauagcu uauugccuac    4560
cuuuuugcug gaaacaaacu gauuugaaaa acaaaaucua ugaagacugc agcuaaggau    4620
uuuaucggua gacuuaagag cuuuugaccu ugguauauu uuagggaac cacaucaguc    4680 ucaauacugu cauuuuacac ugacucagag cagcugacuu cauuccuugc caugauauau    4740
auuuaaggca ggcauuguaa cagacauaaa gacaacuuau cuguuucagc aggaaggauu    4800
caguuuauga acucucagac cagaucaugu ugaacaagga gacuugaug ugugucauga    4860 gaaaacucau ucuuuacuuc ccagucaauu uaaaggccag cuauccgag cuacucgaau    4920 gaaugcacug guuaaacauu ggaaauaguu uguuuauauc cuugucucuc ucuaggccaa    4980
uugugauuac augacucgac ucuacaucuc gucaaacaag gccuaggucu gguugcugua    5040
gacugcucgc cccaacaaa uaaaaucugg uugacuagcc uccuuguaua uacaacuauu    5100
auuuguuaag aagaaauuau cgucaauuuu cuacuaccuu ccaauuguca gcucuuuuu    5160 uccucucugu uuuuuccuau acuuuacaga aaaagacauu gaucuauacu gccauucccu    5220
cuaauccugc cauacucagu caaaaggaau gacuaagau gaagaugauc aucugcucga    5280
gucuaaaaua uacauuguau auaagaauug gugauuagaa aagcaaaaaa ccuaaaacuu    5340
aaaucuagga gucuguauac ugucuccaug ucccaugcc ucagaucuca ucuaaaucuu    5400
ugaacagcac cauucaacca aucgaggcc uugacuugcu uguaagauga uucucagaga    5460
ucggcugagu uaaaaagau gacgacuuga uuaccaaaga aaguagggcc aacuuugaca    5520
aaucuggcuc ugcugacccu gucacuccca gauuagcau agacuccuaa acagaaccuc    5580
aagucugauu gaggauaagg ccuucuccug agcugaaagu ucuuuggcag augagcaaga    5640
aacugaaagc ugauguaccu gacuggcucu guaagaucag aaaacuguau ccagaauaag    5700
cccuauggau uaaccccuga guaccagag uaaaaacuaa uuuacagaac uuccuuauug    5760
aucugcuggu ucuuccagau cauauucugg cuauugguau ggcuggccuu ucugaaggua    5820
cccugcuugu cuauuuccu gacucagcuc uugccugccu uuuucacaug uugcugcaau    5880
uagacucacc gugaggacua cagcaauuu cagucuaucu ugugcccaau acaacaagga    5940
uuuuuaauag uaacaaccca caccucaccc acuaggacuc aauguucaca acaggaagga    6000 ccaugcugc auacuccuug accagcaacu uuuugaaga uauuuuaag ugcagaguag    6060 gccucuauuc cuguauguaa uugucauuu ucagcaccug gaaccucauc uaucggqucu    6120 ggaaggaaua cagcaguucg aaagccgcgu ccauuucucu ccuucaguag ugcagaaaug    6180
aguccgauuc accaguacac acagaacugu accaguucaa ccuagcaaaa gaagaaaagu    6240
uuccacugua cuuaaaauuu acagcugacu caaauugccu cacagaauua uuugauguag    6300
aaggcuaguu gucuuacuuc agaucagcag gacaguuggg cucucagacu caugaccacu    6360
```

-continued

```
gaguuugcuuu guguugaaac uguggauuuca uccaacauau gcuauuggac augauuauua   6420
uuccauucaa auggauuaca gacuucuuga ggacaggaca aacuuaucuc ucauggugu      6480 uuuuuagaau acuuuuauaa ccaaggaaga aaccaugcca gcuguuacca uucaacuucu     6540
uaagcagaga uuaagcuuuu ucauaucugu ucuuauccug gacaucagua guuuuuaauu     6600
gcccagcauc cguuccaucu guaacaacu cccugauguu ucuuaaaacc accucuuccu      6660
auuuucaguc uguggguuugg acagucugac ccaaccuuga gcuuugugg ugaacaugua     6720 auucagaccu caucaaucag caaauccauc ugaacugugg aggagaagcu cucuuuacug     6780
agggugcuuu agcuuuguag gaugaaaacc ucaaacuaac agggccuacc auguagagaa     6840
ugaagccagu gcaggggaaa gcagagccaa aauauggaga gacuugaauc cugaugacag     6900
cguuugugcc ccuggaucca accgugccug aagcuagaau auccccugga cuuuucaguu    6960
augugaacca auaaauaccc uuuuugcuu aaguuacuuu gaguugggu ucuguuacuu      7020 gaaauugaau ccacacuaau auaucuacca acauugagac uugacagauc caaguauuua    7080
uuaagcuaga ggucaugguc acugaaauua cuuuccaaag uggaagacaa aaugaaacag    7140
gaacugaggg aauauuuaag aucccacaga agcguaaaaa ugacauggua gaaaguaaua    7200
gaaaaccuaa augucuguca uuaaaggaua gguuaaggug ugguucagcc auauaggaau    7260
aucucguauc uguuaaaaug aauaaaguac auucauugug uauggaaaaa uggccaugau    7320
acauuaggug aaacaaguua uuaauagaaa aguguacagu gugaacucau uuuaaaaugu    7380
gugugcuuau guuuauaaau gcauagaaag gucuauucac agcuuucuuu gaacagugua    7440
gaucacauga aacuuucaac uuuauacauu ucuguauuaa uauuuuacac uacccacauu    7500
auuuuuaaac uuuauuuuaa auaaagaauu uuuaaaauua aa                      7542

<210> SEQ ID NO 4
<211> LENGTH: 19
<212> TYPE: RNA
<213> ORGANISM: Artificial
<220> FEATURE:
<223> OTHER INFORMATION: siRNA for human TUG1

<400> SEQUENCE: 4
ccagaagagu uaagaauca                                                   19

<210> SEQ ID NO 5
<211> LENGTH: 19
<212> TYPE: RNA
<213> ORGANISM: Artificial
<220> FEATURE:
<223> OTHER INFORMATION: siRNA for human TUG1

<400> SEQUENCE: 5
gugcagaagc ccagaguaa                                                   19

<210> SEQ ID NO 6
<211> LENGTH: 21
<212> TYPE: RNA
<213> ORGANISM: Artificial
<220> FEATURE:
<223> OTHER INFORMATION: siRNA for human TUG1

<400> SEQUENCE: 6
ggauauagcc agagaacaau u                                                21

<210> SEQ ID NO 7
```

<211> LENGTH: 21
<212> TYPE: RNA
<213> ORGANISM: Artificial
<220> FEATURE:
<223> OTHER INFORMATION: siRNA for human TUG1

<400> SEQUENCE: 7
guuaagaaga aauuaucguc a                                              21

<210> SEQ ID NO 8
<211> LENGTH: 21
<212> TYPE: RNA
<213> ORGANISM: Artificial
<220> FEATURE:
<223> OTHER INFORMATION: siRNA for human TUG1

<400> SEQUENCE: 8
ggauuuuuua guuauuaaug c                                              21

<210> SEQ ID NO 9
<211> LENGTH: 21
<212> TYPE: RNA
<213> ORGANISM: Artificial
<220> FEATURE:
<223> OTHER INFORMATION: siRNA for human TUG1

<400> SEQUENCE: 9
cucaaaugau ugaaauucau g                                              21

<210> SEQ ID NO 10
<211> LENGTH: 21
<212> TYPE: RNA
<213> ORGANISM: Artificial
<220> FEATURE:
<223> OTHER INFORMATION: siRNA for human TUG1

<400> SEQUENCE: 10
ccuguuuuuu cuacuucaaa u                                              21

<210> SEQ ID NO 11
<211> LENGTH: 21
<212> TYPE: RNA
<213> ORGANISM: Artificial
<220> FEATURE:
<223> OTHER INFORMATION: siRNA for human TUG1

<400> SEQUENCE: 11
cacaaaugua agaaauucua c                                              21

<210> SEQ ID NO 12
<211> LENGTH: 19
<212> TYPE: RNA
<213> ORGANISM: Artificial
<220> FEATURE:
<223> OTHER INFORMATION: siRNA for human TUG1

<400> SEQUENCE: 12
ugauucuuaa cucuucugg                                                 19

<210> SEQ ID NO 13
<211> LENGTH: 19
<212> TYPE: RNA
<213> ORGANISM: Artificial
<220> FEATURE:
<223> OTHER INFORMATION: siRNA for human TUG1

<400> SEQUENCE: 13
uuacucuggg cuucugcac                                               19

<210> SEQ ID NO 14
<211> LENGTH: 21
<212> TYPE: RNA
<213> ORGANISM: Artificial
<220> FEATURE:
<223> OTHER INFORMATION: siRNA for human TUG1

<400> SEQUENCE: 14
uuguucucug gcuauauccc a                                            21

<210> SEQ ID NO 15
<211> LENGTH: 21
<212> TYPE: RNA
<213> ORGANISM: Artificial
<220> FEATURE:
<223> OTHER INFORMATION: siRNA for human TUG1

<400> SEQUENCE: 15
acgauaauuu cuucuuaaca a                                            21

<210> SEQ ID NO 16
<211> LENGTH: 21
<212> TYPE: RNA
<213> ORGANISM: Artificial
<220> FEATURE:
<223> OTHER INFORMATION: siRNA for human TUG1

<400> SEQUENCE: 16
auuaauaacu aaaaaauccc c                                            21

<210> SEQ ID NO 17
<211> LENGTH: 21
<212> TYPE: RNA
<213> ORGANISM: Artificial
<220> FEATURE:
<223> OTHER INFORMATION: siRNA for human TUG1

<400> SEQUENCE: 17
ugaauuucaa ucauuugaga u                                            21

<210> SEQ ID NO 18
<211> LENGTH: 21
<212> TYPE: RNA
<213> ORGANISM: Artificial
<220> FEATURE:
<223> OTHER INFORMATION: siRNA for human TUG1

<400> SEQUENCE: 18
uugaaguaga aaaaacaggg u                                            21

<210> SEQ ID NO 19
<211> LENGTH: 21
<212> TYPE: RNA
<213> ORGANISM: Artificial
<220> FEATURE:
<223> OTHER INFORMATION: siRNA for human TUG1

<400> SEQUENCE: 19
agaauuucuu acauuugugu a                                            21

<210> SEQ ID NO 20
<211> LENGTH: 19
<212> TYPE: DNA

```
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(17)

<400> SEQUENCE: 20
ccagaagagu uaagaauca                                                    19

<210> SEQ ID NO 21
<211> LENGTH: 19
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(17)

<400> SEQUENCE: 21
gugcagaagc ccagaguaa                                                    19

<210> SEQ ID NO 22
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 22
ggauauagcc agagaacaat t                                                 21

<210> SEQ ID NO 23
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 23
guuaagaaga aauuaucguc a                                                 21

<210> SEQ ID NO 24
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 24
ggauuuuuua guuauuaaug c                                                 21

<210> SEQ ID NO 25
<211> LENGTH: 21
<212> TYPE: DNA
<213> ORGANISM: Artificial
<220> FEATURE:
<223> OTHER INFORMATION: siRNA for human TUG1
<220> FEATURE:
```

```
<221> NAME/KEY: misc_RNA
<222> LOCATION: (1)..(19)

<400> SEQUENCE: 25
cucaaaugau ugaaauucat g                                              21

<210> SEQ ID NO 26
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 26
ccuguuuuuu cuacuucaaa t                                              21

<210> SEQ ID NO 27
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 27
cacaaaugua agaaauucua c                                              21

<210> SEQ ID NO 28
<211> LENGTH: 19
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(17)

<400> SEQUENCE: 28
ugauucuuaa cucuucugg                                                 19

<210> SEQ ID NO 29
<211> LENGTH: 19
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(17)

<400> SEQUENCE: 29
uuacucuggg cuucugcac                                                 19

<210> SEQ ID NO 30
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 30
```

-continued uuguucucug gcuauauccc a                                              21

<210> SEQ ID NO 31
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 31
acgauaauuu cuucuuaaca a                                              21

<210> SEQ ID NO 32
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 32
auuaauaacu aaaaaauccc c                                              21

<210> SEQ ID NO 33
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 33
ugaauuucaa ucauuugaga t                                              21

<210> SEQ ID NO 34
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 34
uugaaguaga aaaaacaggg t                                              21

<210> SEQ ID NO 35
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 35
agaauuucuu acauuugugt a                                              21

```
<210> SEQ ID NO 36
<211> LENGTH: 19
<212> TYPE: RNA
<213> ORGANISM: Artificial
<220> FEATURE:
<223> OTHER INFORMATION: LNA-modified antisense RNA
<220> FEATURE:
<221> NAME/KEY: misc_feature
<222> LOCATION: (1)..(4)
<223> OTHER INFORMATION: locked nucleic acid
<220> FEATURE:
<221> NAME/KEY: misc_feature
<222> LOCATION: (16)..(19)
<223> OTHER INFORMATION: locked nucleic acid

<400> SEQUENCE: 36
uuacucuggg cuucugcac                                                    19

<210> SEQ ID NO 37
<211> LENGTH: 19
<212> TYPE: RNA
<213> ORGANISM: Artificial
<220> FEATURE:
<223> OTHER INFORMATION: LNA-modified antisense RNA
<220> FEATURE:
<221> NAME/KEY: misc_feature
<222> LOCATION: (1)..(3)
<223> OTHER INFORMATION: locked nucleic acid
<220> FEATURE:
<221> NAME/KEY: misc_feature
<222> LOCATION: (17)..(19)
<223> OTHER INFORMATION: locked nucleic acid

<400> SEQUENCE: 37
uuacucuggg cuucugcac                                                    19

<210> SEQ ID NO 38
<211> LENGTH: 19
<212> TYPE: RNA
<213> ORGANISM: Artificial
<220> FEATURE:
<223> OTHER INFORMATION: LNA-modified antisense RNA
<220> FEATURE:
<221> NAME/KEY: misc_feature
<222> LOCATION: (1)..(4)
<223> OTHER INFORMATION: locked nucleic acid
<220> FEATURE:
<221> NAME/KEY: misc_feature
<222> LOCATION: (17)..(19)
<223> OTHER INFORMATION: locked nucleic acid

<400> SEQUENCE: 38
uuacucuggg cuucugcac                                                    19

<210> SEQ ID NO 39
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 39
uacuguuucu uuaaauggcg g                                                 21

<210> SEQ ID NO 40
<211> LENGTH: 21
<212> TYPE: DNA
<213> ORGANISM: Artificial
```

<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 40
aaaaguuuag cuuugaauca c                                              21

<210> SEQ ID NO 41
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 41
auaaaugcau cuugauaugt t                                              21

<210> SEQ ID NO 42
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 42
auuaauaacu aaaaaauccc c                                              21

<210> SEQ ID NO 43
<211> LENGTH: 19
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(17)

<400> SEQUENCE: 43
gaauaagccc uaggauta                                                  19

<210> SEQ ID NO 44
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 44
uaacuuaagc aaaaaagggt a                                              21

<210> SEQ ID NO 45
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA -continued

```
<222> LOCATION: (1)..(19)

<400> SEQUENCE: 45
gccauuuaaa gaaacaguac c                                              21

<210> SEQ ID NO 46
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 46
gauucaaagc uaacuuuut c                                               21

<210> SEQ ID NO 47
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 47
cauaucaaga ugcauuuaut a                                              21

<210> SEQ ID NO 48
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 48
ggauuuuuua guuauuaaug c                                              21

<210> SEQ ID NO 49
<211> LENGTH: 19
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(17)

<400> SEQUENCE: 49
uaauccauag ggcuuautc                                                 19

<210> SEQ ID NO 50
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 50
```

```
cccuuuuuug cuuaaguuac t                                              21

<210> SEQ ID NO 51
<211> LENGTH: 21
<212> TYPE: RNA
<213> ORGANISM: Artificial
<220> FEATURE:
<223> OTHER INFORMATION: LNA-modified antisense RNA
<220> FEATURE:
<221> NAME/KEY: misc_feature
<222> LOCATION: (1)..(4)
<223> OTHER INFORMATION: locked nucleic acid
<220> FEATURE:
<221> NAME/KEY: misc_feature
<222> LOCATION: (18)..(21)
<223> OTHER INFORMATION: locked nucleic acid

<400> SEQUENCE: 51
ugaauuucaa ucauuugaga u                                              21

<210> SEQ ID NO 52
<211> LENGTH: 21
<212> TYPE: RNA
<213> ORGANISM: Artificial
<220> FEATURE:
<223> OTHER INFORMATION: LNA-modified antisense RNA
<220> FEATURE:
<221> NAME/KEY: misc_feature
<222> LOCATION: (1)..(3)
<223> OTHER INFORMATION: locked nucleic acid
<220> FEATURE:
<221> NAME/KEY: misc_feature
<222> LOCATION: (19)..(21)
<223> OTHER INFORMATION: locked nucleic acid

<400> SEQUENCE: 52
ugaauuucaa ucauuugaga u                                              21

<210> SEQ ID NO 53
<211> LENGTH: 21
<212> TYPE: RNA
<213> ORGANISM: Artificial
<220> FEATURE:
<223> OTHER INFORMATION: LNA-modified antisense RNA
<220> FEATURE:
<221> NAME/KEY: misc_feature
<222> LOCATION: (1)..(4)
<223> OTHER INFORMATION: locked nucleic acid
<220> FEATURE:
<221> NAME/KEY: misc_feature
<222> LOCATION: (19)..(21)
<223> OTHER INFORMATION: locked nucleic acid

<400> SEQUENCE: 53
ugaauuucaa ucauuugaga u                                              21
```